(12) United States Patent
Summers et al.

(10) Patent No.: US 6,190,867 B1
(45) Date of Patent: Feb. 20, 2001

(54) METHODS AND MEANS RELATING TO QUIESCENT CELLS AND USES THEREOF

(75) Inventors: David Keith Summers; Duncan Christopher David Rowe, both of Cambridge (GB)

(73) Assignee: Cambridge Microbial Technologies, Ltd., Guildford (GB)

( * ) Notice: Under 35 U.S.C. 154(b), the term of this patent shall be extended for 0 days.

(21) Appl. No.: 09/142,809

(22) PCT Filed: Mar. 17, 1997

(86) PCT No.: PCT/GB97/00731

§ 371 Date: Jan. 22, 1998

§ 102(e) Date: Jan. 22, 1998

(87) PCT Pub. No.: WO97/34996

PCT Pub. Date: Sep. 25, 1997

(30) Foreign Application Priority Data

Mar. 15, 1996 (GB) .................................................. 9605453

(51) Int. Cl.⁷ ...................................................... C12Q 1/68
(52) U.S. Cl. .............................. 435/6; 435/69.1; 435/476; 435/252.3; 435/252.33
(58) Field of Search ........................... 435/252.3, 252.33, 435/320.1, 91.1, 91.4, 971, 476, 489, 243, 6, 69.1

(56) References Cited

FOREIGN PATENT DOCUMENTS

| 0 502 637 | 9/1992 | (EP) . |
| 0 258 118 | 3/1998 | (EP) . |
| WO 93/01293 | 1/1993 | (WO) . |

OTHER PUBLICATIONS

Patient et al. Mol. Microbiol. vol. 9, pp. 1089–1095, 1993.*
Chew et al., *J Biotech.*, 13:47–60 (1990).
Frey et al., *Gene*, 35:103–111 (1985).
Leung et al., *DNA*, 4:351–355 (1985).
Patient et al., *Mol. Microbiol.*, 9:1089–1095 (1993).
Ussery et al., *Biochimie*, 76:968–980 (1994).

* cited by examiner

*Primary Examiner*—Remy Yucel
(74) *Attorney, Agent, or Firm*—Banner & Witcoff, Ltd.

(57) ABSTRACT

The invention features a bacterial cell containing an extra-chromosomal vector that includes an inducible rcd gene, wherein the cell, when placed in broth culture, enters quiescence on expression of the rod gene.

35 Claims, 13 Drawing Sheets

SEQ ID NO:4

Fig 4a

Plac-64mer (SEQ ID NO:5)
5'-ATGCATATGGCTTGACAATTGTGAGCGATAACAATTATAATGTGTGGAGGCG
CGATCGCGGCAG-3'

Plac/lacO/Cer-49mer (reverse) (SEQ ID NO:6)
5'-ATGCATATGAATTTGTGAGCGATAAGAATTGATTTACCATAATCCCTTA-3'

λ $P_R$-75mer (SEQ ID NO:7)
5'-ATGCATATGTAACACCGTGCGTGTTGACTATTTTACCTCTGGCGGTGATAATG
GTTGCAGGCGCGATCGCGGCAG-3' cer-24mer (reverse) (SEQ ID NO:8)
5'-ATGCATATGATTTACCATAATCCC-3'

Fig 4b

Plac-Rcd dsDNA Sequence with 64/49mer primers (SEQ ID NO:9)

5'-ATGCATATGGCTTGACAATTGTGAGCGATAACAATTATAATGTGTGG
3'-TACGTATACCGAACTGTTAACACTCGCTATTGTTAATATTACACACC

AGGCGCGATCGCGGCAGTTTTTCGGGTGGTTTGTTGCCATTTTTACC
TCCGCGCTAGCGCCGTCAAAAAGCCCACCAAACAACGGTAAAAATGG

TGTCTGCTGCCGTGATCGCGCTGAACGCGTTTTAGCGGTGCGTACAAT
ACAGACGACGGCACTAGCGCGACTTGCGCAAAATCGCCACGCATGTTA

TAAGGGATTATGGTAAATCAATTGTTATCGCTCACAAAATCATATGCAT-3'
ATTCCCTAATACCATTTAGTTAACAATAGCGAGTGTTTTAGTATACGTA-5'

Plac-Rcd dsDNA Sequence with 64/24mer primers (SEQ ID NO:10)

5'-ATGCATATGGCTTGACAATTGTGAGCGATAACAATTATAATGTGTGG
3'-TACGTATACCGAACTGTTAACACTCGCTATTGTTAATATTACACACC

AGGCGCGATCGCGGCAGTTTTTCGGGTGGTTTGTTGCCATTTTTACC
TCCGCGCTAGCGCCGTCAAAAAGCCCACCAAACAACGGTAAAAATGG

TGTCTGCTGCCGTGATCGCGCTGAACGCGTTTTAGCGGTGCGTACAAT
ACAGACGACGGCACTAGCGCGACTTGCGCAAAATCGCCACGCATGTTA

TAAGGGATTATGGTAAATCATATGCAT-3'
ATTCCCTAATACCATTTAGTATACGTA-5'

λ P$_R$-Rcd dsDNA Sequence with 75/24mer primers (SEQ ID NO:11)

5'-ATGCATATGTAACACCGTGCGTGTTGACTATTTTACCTCTGGCGGTGA
3'-TACGTATACATTGTGGCACGCACAACTGATAAAATGGAGACCGCCACT

TAATGGTTGCAGGCGCGATCGCGGCAGTTTTTCGGGTGGTTTGTTGCCA
ATTACCAACGTCCGCGCTAGCGCCGTCAAAAAGCCCACCAAACAACGGT

TTTTTACCTGTCTGCTGCCGTGATCGCGCTGAACGCGTTTTAGCGGTG
AAAAATGGACAGACGACGGCACTAGCGCGACTTGCGCAAAATCGCCAC

CGTACAATTAAGGGATTATGGTAAATCATATGCAT-3'
GCATGTTAATTCCCTAATACCATTTAGTATACGTA-5'

METHODS AND MEANS RELATING TO QUIESCENT CELLS AND USES THEREOF

The present invention relates to cells in culture. In particular, it relates to bacterial cells in broth culture which may produce a heterologous (cloned) gene product, and synchronisation of cell division. Methods and means are provided for inducing and capitalising on quiescence of cells.

The development of recombinant DNA technology over the last 20 years has made it possible to identify and isolate genes from any organism and express products in bacteria (the most common host organism is the enteric bacterium *Escherichia coli*). To achieve this, the gene is first inserted into a vector and then introduced into the bacterium by a method such as transformation or electroporation. Cloning and expression vectors are generally derivatives of plasmids: autonomously-replicating DNA circles which are found extensively in natural populations of bacteria. Typically, vectors carry some kind of marker to facilitate selection of vector-containing cells (for example an antibiotic resistance gene) and expression signals which direct the host bacterium to synthesise exogenous genes.

A number of factors may reduce the efficiency with which the products of cloned genes are expressed in a bacterial host:

Many plasmid cloning vectors have copy numbers far in excess of that of their naturally occurring progenitors. For example, natural plasmid ColE1 has a copy number of 20–30 compared with 100–200 for vector pUC18. This increase in DNA loading on the cell gives a selective advantage to any cell which loses the plasmid and means that plasmid-free cells accumulate rapidly in the culture.

If the product gene is expressed constitutively (i.e. throughout the growth of the culture) or if it is expressed from an inducible promoter which cannot be turned off completely during the early stages of culture growth (which is a common situation) there will be even more metabolic demands placed upon plasmid-bearing cells. This will give an advantage to plasmid-free cells or to cells containing rearranged vectors which no longer express the product gene. If these arise early in the culture, the consequences for productivity will be serious. One solution to these problems is to arrange for vector copy number to be low initially and to increase when expression of the product gene is required. It is, for example, possible to increase copy number by down-regulating synthesis of the replication inhibitor or by up-regulating synthesis of an initiator protein (Rep) or replication primer.

Present technology requires that cloned genes are expressed in actively-growing cells. The cellular machinery required for transcription and translation of the recombinant gene is required also for the expression of genes essential for the growth of the host cell. Furthermore, the economy of the cell is devoted largely to the creation of biomass. There is thus a conflict between the requirements of the biotechnologist and the bacterium.

The metabolic stress imposed by the expression of a recombinant gene invariably reduces the growth rate and viability of the host cell. The higher the copy number of the cloning vector and the expression level of the cloned gene, the greater the effect. Cells which have lost the cloning vector or have deleted or rearranged the cloned gene will almost invariably out-grow the original cell-type, reducing yield and purity of the product.

In addition to problems arising from the metabolic load placed upon the cells by the need to replicate the plasmid and to transcribe and translate its genes, the cloned gene product may be toxic to the host cell or interfere with its growth and division. An illustration of this phenomenon is provided by the *E. coli* LacY permease which is responsible for transport of lactose across the cell membrane. Over-expression of LacY is lethal to the cell. Similar problems are likely to be experienced if membrane proteins from any source are expressed in a bacterial host. Problems might also arise if the product of the cloned gene interferes with replication of the bacterial chromosome, transcription of genes essential to the growth and division of the host cell, or disrupts other vital processes. Many adverse effects on growth of the bacterial host may be avoided if the protein is expressed in non-growing (quiescent) cells.

Expression of the cloned gene is simultaneous with the expression of thousands of genes located on the host chromosome. The recombinant product is therefore likely to represent a relatively small part of total cell protein, especially if the copy number of the cloning vector is not very high or if the product of the cloned gene is harmful to the host bacterium.

An aspect of the present invention utilises viable but quiescent (non-growing) cells in which the expression of chromosomal genes is repressed but expression of vector-(e.g. plasmid-) borne genes is allowed.

To our knowledge there has been no previous serious attempt to use quiescent cells as factories for the production of recombinant gene products. Pre-existing methods to inhibit cell growth almost invariably have undesirable side effects such as induction of the SOS response (which increases the mutation rate and causes cell filamentation) or interference with aspects of host metabolism which are required for expression of the cloned gene.

The present invention in various embodiments makes use of the rcd gene transcript of *E. coli* plasmid ColE1 or the equivalent from another bacterium or plasmid. The rcd transcript is produced in nature by expression from a promoter ($P_{cer}$) within the cer site of dimerised ColE1 plasmids (Patient & Summers, 1993; FIG. 1). It is one of the ways by which ColE1 achieves a high degree of stability in a population of cells.

The formation of plasmid multimers (through intermolecular recombination) is a major cause of instability of high copy number plasmids and cloning vectors (Summers, 1991) and therefore a further problem for the biotechnologist. Multimerisation reduces the plasmid copy number and, because the plasmids are distributed randomly between the daughter cells, it increases the frequency at which plasmid-free cells arise. A dividing cell containing 40 plasmid monomers has a probability of $10^{-12}$ of producing a plasmid-free daughter. In a cell which contains 20 dimers the probability is increased one million fold to $10^{-6}$. Plasmid-free cells typically grow faster than those carrying plasmids and, as a result, the production of a few plasmid-free cells can be followed rapidly by the virtual disappearance of plasmid-containing cells. Such "segregational instability" can be a serious problem in large-scale culture where it is impractical to maintain a plasmid by selective pressure (e.g. by the addition of antibiotics to the culture medium).

Some natural plasmids are extremely stable compared with the majority of man-made cloning vectors. ColE1 (the plasmid upon which many cloning vectors are based) achieves its stability in a population of cells by action of three systems:

(a) Colicin Production. ColE1 carries a gene for the toxic colicin E1 protein (which is synthesised by bacteria and released into the growth medium) and a second gene which confers immunity to colicin. Cells which lose the plasmid are susceptible to killing by exogenous colicin because they cannot produce the "antidote" to the toxin. Cells which retain the plasmid are immune to the killing effect of the toxin.

(b) Conversion of Multimers to Monomers. Multimers are resolved to monomers by site-specific recombination. This process requires a 250 bp section of DNA in the plasmid (the cer site; Summers & Sherratt, 1984) and at least four proteins encoded by the host bacterium (XerC, XerD, ArgR and PepA). Recombination is unidirectional i.e. it converts dimers to monomers but not vice versa.

(c) Growth Inhibition of Multimer Containing Cells. It has been shown that plasmid dimers replicate at twice the rate of monomers because they contain two replication origins. As a direct consequence, if a single plasmid dimer is formed by homologous recombination, dimer-only cells will appear among the descendants of this unfortunate cell within a few generations (Summers et al, 1993). Dimer-containing cells have a reduced number of plasmid copies and are therefore at risk of producing plasmid-free offspring.

The presence of dimers in a cell triggers the expression of the rcd gene from its promoter ($P_{cer}$) within the cer site. The resulting Rcd RNA transcript (Patient & Summers, 1993; FIG. 2 herein) is an inhibitor of cell division. A notable feature of $P_{cer}$ in nature is that it is produced at elevated level in cells which contain plasmid multimers; the transcript is not detected at high levels in cells which contain only plasmid monomers. Rcd thus inhibits the division of those cells most at risk of producing plasmid-free offspring.

Rcd is the first plasmid-encoded transcript which has been shown to interfere with bacterial cell cycle. Superficially there is some resemblance to host-killing functions identified on low copy number plasmids but fundamental differences are revealed by closer examination. Many host-killing systems have been identified (e.g. ccd of plasmid F (Jaffe et al, 1985) and hok-sok of plasmid R1 (Gerdes et al, 1990)) and they all prevent the proliferation of plasmid-free cells in similar ways. The plasmid encodes both a poison and an antidote. The poison is long-lived but the antidote turns over rapidly so that in a plasmid-free cell the antidote disappears and the cell succumbs to the poison. The two fundamental differences between host-killing and rcd are (1) that the latter prevents the formation of plasmid-free cells while the former acts only after plasmid-free cell has been formed and (2) cells in which a host killing system has been activated, die. The loss of viability makes host killing systems unsuitable for the production of quiescent cells envisaged in this application. In contrast, Rcd does not kill cells and its effect on cell growth has been shown to be reversible. For instance, it has been observed that cells on agar plates which cannot form colonies due to Rcd expression, form normal colonies when expression is switched off. The longer cells are held in quiescence, the more difficult it is to get them out again.

The present inventors have realised that the effects of rcd transcription are useful in a number of ways to alleviate, at least partially, known problems in the art. Rcd-like transcripts of bacteria other than E. coli should be useful in similar ways. Experimental work demonstrating the ability of expression of heterologous rcd to inhibit severely the growth of host cells in plated culture has previously been reported [Patient & Summers, 1993].

When E. coli DS941 [Summers & Sherratt, 1988] containing a plasmid with rcd under the control of a temperature-sensitive mutant of the $P_{cer}$ promoter ($P^+_{cer}$) is grown on L-agar plates at 42° C., colony formation is blocked. The mutant derivative of the $P_{cer}$ promoter ($P^+_{cer}$) is no longer under monomer-dimer control and produces an elevated level of Rcd [Patient & Summers, 1993]. This promoter is naturally temperature sensitive with transcription increasing 5 to 10-fold between 30 and 42° C. Its sequence is TTGTTGcataggtattcatacggTAAAAT (SEQ ID NO. 1).

Surprisingly, however, on minimal agar, growth of these same cells is normal. Likewise in L-broth culture, the culture conditions most of interest to biotechnologists wishing to produce large quantities of cloned gene product, growth is normal at 42° C.

There are significant differences between the physiology of bacterial cells growing on agar and in broth culture. In particular, cells in broth can achieve exponential growth while this is very unlikely to occur when cells are forming colonies on a solid substrate. We believed that medium-related changes in cell physiology might be responsible for the loss of Rcd sensitivity in broth culture.

A number of DNA binding proteins have been shown to vary in concentration between periods of exponential growth and stationary phase in broth culture. It is thought that these might act as global regulators and modulate gene expression in order to adapt the cell to changes in growth conditions. Candidates for this role include FIS (Finkel et al, 1992) and H-NS (Ussery et al, 1994). The concentration of FIS falls in stationary phase and we thought that this might also be the case for cells growing on solid media. If a high level of FIS somehow overcomes the effect of Rcd on cell division in exponential phase, fis cells might be sensitive to Rcd in broth culture. We therefore tested the effect of inducing Rcd in DS941 fis cells growing in L-broth. The fis mutations appeared to result in only a slight increase in sensitivity to Rcd and although there was a reduction of the growth rate for mutant cells growing in broth culture, they did not enter a non-growing (quiescent) state.

Some workers have reported that H-NS concentration increases as cells enter stationary phase. Cells growing on solid media might therefore be expected to have elevated H-NS concentration which might make them more sensitive to Rcd. Over-expression of H-NS in cells growing exponentially in broth culture might be expected to increase their sensitivity to Rcd. Surprisingly we found that the opposite was true. DS941 hns cells growing exponentially in L-broth were sensitive to Rcd. Within 90–120 min of induction of the rcd gene, cell growth stopped completely and the culture density remained constant for up to 20 hours.

The present invention is founded on the discovery that rcd can inhibit the growth of cells in broth culture when the cells are hns$^-$, i.e. lack or have a defective hns gene. Using this discovery and the observation that the chromosomal DNA of cells arrested by rcd expression is highly condensed, while plasmid DNA in the same cells is not condensed and the cells remain viable, the present invention has been made. The roles of H-NS protein are reviewed by Ussery et al (1994). The sequence of H-NS is given in: Pon, et al., *Mol. Gen. Genet.* 212, 199–202. Nomenclature has settle on hns but at some places in the literature the gene is also referred to as: hnsA, bglY, drdX, msyA, osmZ and pilG. Bacteria other than E. coli have H-NS-related proteins for which sequences have been published, for example *S. Flexneri, S. typhimurium, S. marcescens* and *P. vulgaris*. The present invention is not limited to E. coli and may be applied to any bacterial species, so references to hns$^-$ cells should be taken as reference to cells defective or deficient in the relevant hns like gene in the bacteria of interest. Likewise, references to rcd include the equivalents found in other plasmids and in other bacteria, such as *Citrobacter freundii, Salmonella typhimurium* and *Enterobacter cloacae.*

Equivalent genes or homologues in other bacteria may be identified using any of a number of available approaches. H-NS-like proteins may be identified by DNA and/or amino acid sequence similarity to the *E. coli* gene or protein or homologues which have been identified already in other bacteria species (see above). Rcd homologues may also be found by sequence similarity to rcd. rcd-like genes may be found within multimer resolution sites on multicopy plasmids in various bacterial species. On comparison of sequences corresponding to rcd in a variety of multimer resolution sites we have identified a conserved core sequence of 13 bp. This conserved sequence is 5'-CGGGTGGTTTGT-3' (SEQ ID NO. 2).

Nucleic acid and/or amino acid sequence information for HN-S or Rcd or a homologue of either may be used in design of nucleic acid molecules for hybridisation experiments to identify equivalent genes or homologues. Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further, It is well known in the art to increase stringency of hybridisation gradually until only a few positive clones remain.

As an alternative to probing, though still employing nucleic acid hybridisation, oligonucleotides designed to amplify DNA sequences may be used in PCR or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between at least two known or putative homologues. On the basis of amino acid sequence information oligonucleotide probes or primers may be designed, taking into account the degeneracy of the genetic code, and, where appropriate, codon usage of the organism from the candidate nucleic acid is derived.

Preferred nucleic acid sequences suitable for use in the design of probes or PCR primers are sequences conserved (completely, substantially or partly) between at least two known or putative homologues. For instance, a preferred probe or primer comprises the sequence indicated above as conserved between a variety of sequences corresponding to rcd in a variety of multimer resolution sites, or a fragment thereof that retains the requisite hybridisation specificity.

Assessment of whether or not a PCR product corresponds to an H-NS- or Rcd-like gene may be conducted in various ways. A PCR band from such a reaction might contain a complex mix of products. Individual products may be cloned and each one individually screened for activity.

A further method of using a sequence to identify other homologues is to use computer searches of expressed sequence tag (EST) and other DNA sequence databases.

Thus, reference to "an rcd gene" herein may be taken to cover not only rcd of *E. coli*, the transcribed RNA sequence of which is shown in FIG. 2, but also any mutant, allele, variant, derivative or homologue thereof, including one or more of addition, substitution, deletion and insertion of one or more nucleotides. Functionally, for use in the present invention an rcd mutant, allele, variant, derivative or homologue needs, on expression, to be able cause a suitable bacterial cell, such as *E. coli* in broth culture to enter quiescence. Preferred embodiments may include those which are able to cause hns⁻ cells, especially hns⁻ *E. coli* cells, in broth culture to enter quiescence.

An rcd gene may include the 13 nucleotide conserved motif 5'-CGGGTGGTTTGT-3' (SEQ ID NO. 2), or a homologous sequence, for instance a sequence having at least 6 matches with the 13 nucleotide motif, preferably at least 7, 8, 9, 10, 11 or 2 matches. It should be remembered that U is substituted or T in RNA molecules, so an Rcd transcript may include the 13 nucleotides 5'-CGGGUGGUUUGU-3'(SEQ ID NO. 2), or a homologous sequence in the terms indicated. An Rcd transcript may have at least about 50% homology with the transcript sequence shown in FIG. 2, preferably at least about 60%, 70%, 80%, 85%, 90% or 95%.

Wild-type H-NS (the product of the hns gene) antagonises the establishment and/or maintenance of quiescence in bacterial cells in broth on expression of Rcd. Experimental evidence provided herein shows with various hns⁻ alleles, especially truncation alleles, that hns⁻ cells in broth culture enter quiescence on expression of Rcd. The truncated alleles experimentally exemplified herein are hns-205 and hns::Tn10(N43). In both cases the C-terminal part of the H-NS protein is absent due to a transposon insertion in the gene. The 205 allele is described in detail in Dersch, et al., *Mol. Gen. Genet.* (1994) 245, 255–259. The N43 strain was given to us by Prof. I. B. Holland, Université Paris-Sud. The hns-206::Amp allele also used in experiments described herein is described in detail in Dersch, et al., *Mol. Gen. Genet.* (1994) 245, 255–259. In this case there is no detectable protein product.

As noted, the sequence of *E. coli* H-NS is given in Pon et al. (1988) *Mol. Gen. Genet.* 212 199–202. The present invention may utilise down-regulation of or a mutation in this gene in *E. coli* or in an allele or homologue in other bacterium. An allele or homologue may share a certain level of homology with the sequence of *E. coli* H-NS. Homology may be at the nucleotide sequence and/or amino acid sequence level. Preferably, the nucleic acid and/or amino acid sequence shares homology with the sequence encoded by the nucleotide sequence of *E. coli* H-NS, preferably at least about 50%, or 60%, or 70%, or 80% homology, most preferably at least 90% or 95% homology. The wild-type gene shares with the *E. coli* gene the ability to antagonise the establishment and/or maintenance of quiescence in a bacterial cell, e.g. an *E. coli* cell, in broth culture on expression of Rcd from an extrachromosomal vector. A mutant of the wild-type that abolishes, wholly or partially, this ability may be useful in the present invention.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Homology may be over the full-length of the H-NS sequence, or may more preferably be over a contiguous sequence of amino acids e.g. about 20, 25, 30, 40, 50 or more amino acids compared with the sequence of Pon et al. At the nucleic acid level, homology may be over the full-length length or may more preferably be over a contiguous sequence of nucleotides, e.g. about, 50, 60, 70, 75, 80, 90, 100, 120, 150 or more nucleotides.

Without wishing to be bound by theory, it can be hypothesized that H-NS is required for recovery of cells from Rcd growth inhibition, such that over-expression of Rcd in an hns mutant background pushes the cells into a non-growing state from which they have no escape. Disruption of other cellular components which normally antagonise the establishment and/or maintenance of quiescence in bacterial cells in broth on expression of Rcd may be used in embodiments of the various aspects of the present invention instead of hns⁻.

Mutations which disrupt the antagonistic effect of a cellular component may be screened for by over-expressing Rcd in mutagenised wild-type cells then treating the cells (e.g. two to three hours after Rcd induction) with an antibiotic such as penicillin or other molecule which kills growing cells but not cells which are not growing. Cycling this treatment several times selects for any host cell mutation which increases the severity of Rcd-mediated growth inhibition.

A candidate for a mutation which diminishes an activity which antagonises Rcd-mediated establishment and/or maintenance of quiescence in a bacterial cell in broth culture is an rnc mutation, i.e. RNase III deficiency. RNase III or one or more other endoribonucleases are responsible for Rcd turnover. Reducing the endoribonuclease activity responsible for degrading Rcd may be used to increase levels of Rcd expression and tip the balance towards establishment of quiescence in accordance with the present invention. RNase III cleaves double-stranded RNA and appears to specifically recognize stem-loop structures (Court, 1993). Much work has been done on the factors which make transcripts more or less sensitive to the enzyme (see, for example, Hjalt and Wagner, 1995). RNase E has been shown to cleave several antisense RNAs including RNAI (Tomcsányi and Apirion, 1985) and CopA (Söderbom et al., 1996). The exoribonucleases polynucleotide phosphorylase (PNPase) and RNase II, also have key roles in RNA decay (Donovan and Kushner, 1986). Poly (A) polymerase (PcnB), which catalyzes the template-independent sequential addition of AMP to the 3'-terminal hydroxyl groups of RNA molecules, has also been implicated in degradation of RNAI (the replication inhibitor of plasmid ColE1). RNAI undergoes PcnB-dependent polyadenylation in vivo and is rapidly degraded, subsequent to RNase E cleavage, in the presence of PcnB and PNPase (Xu et al., 1993). If the pcnB gene is inactivated, the processed species is stabilized.

Using a bacterial strain containing a mutation in a cellular component which in wild-type form antagonises the establishment and/or maintenance of quiescence in broth culture on expression or Rcd is one approach in accordance with the present invention. Other ways of antagonising the function or activity of such a cellular component include down-regulation of gene expression, e.g. using antisense technology, a sequence-specific ribozyme or a modified sigma factor.

The essence of a preferred embodiment of one aspect of the invention is that by inducing Rcd synthesis, hns⁻ host cells, or other cells in which an activity which normally antagonises Rcd-mediated establishment of quiescence in bacterial cells in broth culture is abolished, wholly or partially, can in broth culture be switched to a quiescent state in which their growth and division is arrested. In this state the cells may produce predominantly or only the products of vector-encoded genes and with the resources required for high-level expression of extra-chromosomal genes being readily available. This is useful in both preparative and analytical synthesis of the products of cloned genes.

The cell may comprise the vector following transformation of the cell or an ancestor thereof.

According to one aspect of the present invention there is provided a host cell containing a vector comprising an inducible rcd gene, which cell when in broth culture enters quiescence on expression of the rcd gene. A preferred embodiment may employ a hns⁻ cell. Other cellular backgrounds, such as mutations, which reduce, diminish or decrease, wholly or partially, activity of a cellular component which antagonises the establishment of quiescence in a bacterial cell in broth culture on expression of Rcd may be used instead of hns mutant cells. This should be borne in mind when considering the discussion herein that uses hns mutants as a preferred example. Other backgrounds, including other mutations and systems in which activity of a cellular component is antagonised, e.g. using antisense, ribozyme or other techniques at the disposal of the person skilled in the art, may be substituted for hns in the discussion herein.

The cell may have been transformed with the vector. The term "transformation" is intended to cover all ways of introducing nucleic acid vectors into cells.

It is essential that the rcd gene is based on an extra-chromosomal vector such as a plasmid so that it remains transcriptionally active in cells where the chromosome is condensed and inactive. Vectors can be used in which rcd is present as an integral part of a modified cer site. This has additional advantages of structural and segregational stability for the plasmid. A heterologous gene of interest for expression may be cloned into the vector carrying rcd or it may be on a second vector in the host cell. A single vector (e.g. plasmid) system has the advantage of simplicity.

The heterologous (or "exogenous" or "foreign") gene of interest may be inducible or constitutively expressed. The heterologous gene product may be one which has a toxic effect on the cell, particularly one which adversely affects viability or cell growth and/or division. The heterologous gene may be a non-E. coli gene, or if a non-E. coli host cell is employed a gene not of that host, and it may be a eukaryotic gene e.g. mammalian.

In broth culture cells according to the invention can be grown up and rcd expression switched on to induce a quiescent state in which expression of genes on the condensed chromosomal DNA is eliminated, or reduced, compared with prior to rcd expression. Expression of plasmid vector borne genes proceeds in these cells.

Expression of a gene product which has an adverse effect on cell growth and/or division, for example one which interferes with replication of the bacterial chromosome, transcription of one or more genes essential to the growth and division of the host cell, or disrupts one or more other vital processes, is less likely to have an adverse effect on quiescent (non-growing) cells than growing cells.

According to another aspect, the present invention provides a method of expressing a gene heterologous to a cell, comprising:

(a) growing hns⁻ cells in broth culture, the cells containing an inducible extra-chromosomal vector-borne rcd gene and an extra-chromosomal vector comprising the heterologous gene;

(b) inducing rcd expression and causing or allowing expression of the heterologous gene.

The rcd expressing cells should be able to express the heterologous gene which may be induced after rcd expression is induced or may be constitutively expressed.

The method may comprise an additional step of introducing a vector containing an inducible rcd gene into a hns⁻cell. It may comprise a step of introducing a vector comprising nucleic acid encoding the gene of interest with suitable control elements for transcription and translation. The rcd gene and heterologous gene of interest may be on the same vector, and may even be under coordinated control for linked expression. Following production of the heterologous gene product, the method may include any number of conventional purification steps (Harris & Angal, 1989).

The expression product may be isolated and/or purified from cells from the culture or from the broth culture medium. It is conventional in the art to provide recombinant gene products as a fusion with a "signal sequence" which causes-secretion of the product into the growth medium, to facilitate purification. This is one possibility amongst the many known to those skilled in the art.

An isolated and/or purified expression product may be modified and the expression product or a modified form thereof may be formulated into a composition which includes at least one additional component, such as a pharmaceutically acceptable excipient, carrier, buffer, stabiliser or other materials well known to those skilled in the art. Such materials should, for a pharmaceutical composition, be non-toxic and should not interfere with the efficacy of the active ingredient. The precise nature of the carrier or other material will depend on the route of administration.

An expression product may be modified for example by chemical derivatisation or cross-linking to one or more other molecules, including peptides, polypeptides, labelling molecules.

A chemical moiety may be introduced at a specific chemically modifiable residue or residues. For instance, a cysteine residue may be available for chemical modification via its thiol group. Other chemically modifiable amino acids include lysine, glutamate, histidine and tyrosine. Covalent modification allows a wide variety of moieties to be incorporated, particularly reporter groups or cofactors for catalysis. This allows the interaction of large organic groups such as the fluorescent reporter group, 7-nitrobenz-2-oxa-1, 3-diazole (NBD). Other large groups such as the flavin cofactors for catalysis, FMN and FAD may be incorporated.

There are other possible ways of modifying a polypeptide. There are a number of amino acid residues which may be specifically derivatized using molecules containing specific functional groups. For instance, amino groups may be modified with N-hydroxysuccinimide esters, carboxyl groups with carbodiimides, histidines and cysteines with halomethyl ketones, arginine with glyoxals (see e.g. A. R. Fersht, Enzyme Structure and Mechanism 2nd edn, 1985 pp 248–251, W. H. Freeman, New York).

Some reagents which may be used to modify specific amino-acid residues are given by T. Imoto and H. Yamada in "Protein Function: a Practical Approach", pp 247–277, 1989. To introduce specific functional groups into polypeptides the reactive group of these reagents may be combined with the functional group in a modifying reagent. For instance, if it is desired to modify a protein with the fluorophore 7-amino-4-methylcoumarin-3-acetic acid, the N-hydroxysuccinimidyl ester of the molecule may be used to modify amino groups, whereas N-[6-(-amino-4-methylcoumarin-3-acetamido)hexyl]-3'-(2'-pyridyldithio)propionamide may be used to modify cysteine groups.

Another possible methodology is to use transglutaminase which catalyzes an acyl-transfer reaction between the gamma-carboxyamide group of glutamine residues and primary amines (E. Bendixen et al, *J. Biol. Chem.* 26821962–21967, 1993; K. N. Lee et al *Biochim. Biophys. Acta* 1202 1–6 1993; T. Kanaji et al *J. Biol. Chem.* 268 11565–11572 1993). This enzyme could therefore introduce amino acid residues from a peptide into a glutamine residue through a peptide lysine epsilon amino group or into a lysine group via a peptide glutamine group. The enzyme could also catalyse derivatization of glutamine residues with a primary amine.

A further approach is to introduce chemical moieties to either the N or C terminus of a polypeptide using reverse proteolysis or chemical conjugation or a combination of the two (I. Fisch et al, *Bioconj. Chem.* 3, 147–153, 1992; H. F. Gaertner et al, *Bioconjug. Chem.* 3, 262–268, 1992; H. F. Gaertner et al, *J. Biol. Chem.* 269, 7224–7230, 1994; J. Bongers et al, *Biochim. Biophys. Acta*, 50, S57–162, 1991; R. Offord, *Protein Engineering*, 4, 709–710, 1991). These methods have been used to introduce non-encoded elements to protein and peptide molecules.

Examples of fluorophores which may be introduced are fluorescein, phycoerythrin, coumarin, NBD, Texas Red and chelated lanthanide ions. Examples of catalytic groups which may be introduced are flavin adenine dinucleotide (FAD), flavin mononucleotide (FMN), cytochromes and chelated metal ions such as zinc and copper.

Systems for cloning and expression of a polypeptide in a variety of different host cells are well known.

Suitable vectors can be chosen or constructed, containing appropriate regulatory sequences, including promoter sequences, terminators, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual*: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992. The disclosures of Sambrook et al. and Ausubel et al. are incorporated herein by reference.

For bacterial cells, suitable techniques for introducing nucleic acid ("transformation") may include calcium chloride transformation, electroporation and transfection using bacteriophage.

The introduction may be followed by causing or allowing expression from the nucleic acid, e.g. by culturing host cells under conditions for expression of the gene.

The term "inducible" as applied to a gene or more particularly a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

For use in bacterial systems, many inducible promoters are known (Old and Primrose, 1994). Common examples include $P_{lac}$ (IPTG), $P_{tac}$ (IPTG), $\lambda P_R$ (loss of Cl repressor), $\lambda P_L$ (loss of Cl repressor), $P_{trc}$ (IPTG), $P_{trp}$ (IAA). The inducing agent is shown in brackets after each promoter.

When it is appropriate to use a single plasmid system for expression of a heterologous gene in quiescent cells, suitable arrangements of elements of the vector may be as follows.

(a) Use can be made of the $P^+_{cer}$ promoter mutant which is temperature sensitive. Increasing the temperature of the growth medium therefore provides a convenient way to elevate Rcd levels and switch cells into a quiescent state. Furthermore, the copy number of many plasmid cloning vectors such as pUC18/19 plasmid increases at elevated temperature [Xia et al, 1991] thus enhancing the increase in intracellular levels of Rcd.

(b) Another approach is to clone rcd downstream of any inducible promoter (e.g. $P_{lac}$ which is inducible by the addition of 1 mM IPTG to the growth medium).

(c) A further alternative is to use a λP promoter or other promoter induced on loss of a repressor.

FIGS. 3, (a), (b) and (c) shows how elements in a vector may be arranged. Antibiotic resistance provides a convenient marker for selection purposes.

The use of an Rcd-based quiescent cell system in large scale fermenters may have one or more advantages, such as a higher yield of product, a greater purity of product due to lower levels of contamination by host gene products, fewer problems of structural and segregational instability because of the reduced stress on the host cells.

Generally in the art, problems arise when attempting to monitor the products of vector-borne genes, due to the high background of chromosomal gene products. To circumvent these problems, "minicells" and "maxicells" have been used. Both approaches require the use of host cells carrying specific mutations. Minicells are chromosome-less cells produced as a result of asymmetric deposition of the septum (the "cell divider") during cell division. Minicells have to be separated physically from chromosome-containing cells, typically by sucrose gradient centrifugation; a time consuming and technically-demanding procedure. Maxicells carry chromosomal mutations which make them UV-sensitive and are irradiated to fragment the bacterial chromosome; plasmids survive by virtue of their high numbers and their small size. The majority of protein synthesis is therefore from plasmid genes.

An Rcd-based technique offers a simple and effective alternative to minicells and maxicells.

According to another aspect of the invention there is a method of monitoring the production of protein by expression from an extra-chromosomal vector of interest, comprising introducing the vector into host cells containing a vector comprising an inducible rcd gene and growing the cells in culture, inducing rcd expression, causing or allowing expression from the vector of interest and determining the expression from the vector. As discussed at length already above, the cells may be hns⁻ or be otherwise sensitive to establishment of quiescence on induction of Rcd expression in broth culture.

Expression at the polypeptide level may be determined by introducing a suitable label into the cells and determining the incorporation of the label into produced peptides or polypeptides. The method may comprise introducing the label into the culture, causing or allowing expression from the vector of interest, lysing cells from the culture, running the lysate on an SDS-polyacrylamide gel and observing the labelled protein on the gel (FIG. 8).

The labelled amino acid may be $^{35}$S-methionine. Observation of radiolabelled proteins may be by autoradiography.

Expression at the mRNA level may be similarly determined by using a suitable label.

The vector of interest may in principle be introduced into the cells before or after induction of rcd. However, it is preferred that the vector be introduced before rcd induction.

Instead of the above approach, the vector of interest may be engineered to comprise an inducible or constitutive rcd gene before introduction into (e.g.) hns⁻ cells, which cells in such an instance need not contain a vector comprising an rcd gene prior to introduction of the vector of interest. A further alternative is to introduce the cells a vector comprising an rcd gene following introduction of the vector of interest. These two alternative approaches are less preferred (for being more complicated) than the approach wherein the cells already contain a vector comprising an inducible rcd gene.

After Rcd is induced, only genes on extra-chromosomal vectors within the cells, such as plasmids, will be expressed, or predominantly only these genes. The condensation of the chromosomal DNA upon Rcd expression reduces or eliminates expression of chromosomal genes. The protein which can be observed by means of the label will be that produced after "shut-down" of the chromosomes, i.e. that encoded by nucleic acid forming part of an extra-chromosomal vector.

One aspect of the present invention is a method to amplify the copy number of plasmid cloning vectors when cells enter the quiescent state. This reduces the metabolic load imposed on cells during the growth phase and increases the copy number of the vector (and thus of the product gene) during the quiescent state. Many plasmid replication control systems are described by the "+n" model which states that for a plasmid with an average copy number of n in a new-born cell, an average of n replication events will occur per unit time (which is the generation time in a steady state culture), irrespective of actual copy number (Nielsen and Molin, 1984). We have discovered that for cells in the quiescent state, replication of some plasmids continues, despite the cessation of cell growth and division. It is thus possible to employ a low copy number vector which places the minimum stress on its host cells during the growth phase of the culture but which increases in copy number during and after entry into quiescence.

Many scientific investigations, including in vivo studies of DNA replication and cell division, are greatly assisted by synchronising the cells within culture so that all cells undergo division at the same time. Existing procedures are technically-demanding or unreliable, involving the isolation of new-born cells by virtue of their size or using a bacteriostatic agent (e.g. the antibiotic chloramphenicol) to block a key process such as the initiation of chromosomal DNA replication and removing the agent by washing after growth has been halted. The reversibility of the Rcd-mediated block of cell division provides a simple and effective way to achieve synchronisation of cell division and chromosomal DNA replication.

Rcd blocks growth at a specific stage in the cell cycle [Patient & Summers, 19931]; chromosome partitioning is complete but septation has not occurred. The effect is reversible without serious loss of cell viability.

According to a further aspect of the present invention there is provided a method of synchronising cell cycles of cells in broth culture, comprising inducing the expression of an rcd gene carried on an extra-chromosomal vector within (e.g.) hns⁻ cells in broth culture, incubating the cells for a time equivalent to a further two cell cycles at least and removing the inducing signal, thereby switching off rcd expression from the extra-chromosomal vector.

The method may comprise the introduction of an rcd gene bearing vector into the cells.

The present invention further encompasses use of hns⁻ cells in any of the methods described and vectors specially adapted for use in any of the methods.

The invention in various aspects will now be described further by way of exemplification. Figures referred to are as follows.

FIG. 1 shows the structure of the ColE1 cer site. Conversion of plasmid dimers to monomers is accomplished by site-specific recombination at this site. The position of DNA strand exchange is shown by a cross. The $P_{cer}$ promoter is active in plasmid dimers and directs the synthesis of the Rcd transcript, (approximately 80 bases).

FIG. 3(a) shows elements in a vector where rcd is expressed from an up-promoter derivative of the $P_{cer}$ promoter.

FIG. 3(b) shows the elements of a vector from which rcd is expressed from $P_{lac}$.

Figure 3:
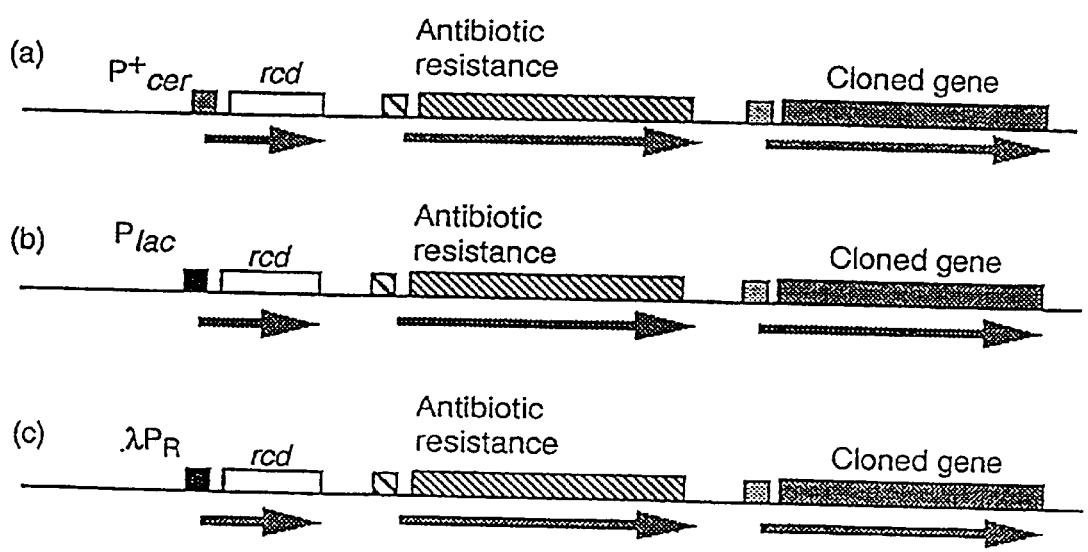
FIGS. 3A–3C shows linear maps of plasmid vectors.

FIG. 3(c) shows the elements of a vector from which rcd is expressed from $\lambda P_R$. Antibiotic resistance provides a convenient marker for selection purposes. Square boxes represent promoters and arrows indicate transcripts.

FIGS. 4A and 4B illustrates the construction of Rcd expression cassettes.

FIG. 4a shows the single stranded DNA primers used to generate the expression cassettes by PCR (polymerase chain reaction) using the cer site as a template.

FIG. 4b illustrates expression cassettes constructed by PCR in which rcd is transcribed from $P_{lac}$ or $\lambda P_R$.

FIGS. 5A and 5B illustrate two plasmids which have been used to induce quiescence.

FIG. 5a shows plasmid B8, a 2915 bp plasmid which carries the rcd gene under the control of $\lambda P_R$.

FIG. 5b shows plasmid pCI857, a 4182 bp plasmid with a compatible origin for ColE1 plasmids in which transcription of rcd is regulated by the cI857 repressor which is expressed constitutively. The selectable marker in pCI857 is kanamycin resistance.

Figure 6:
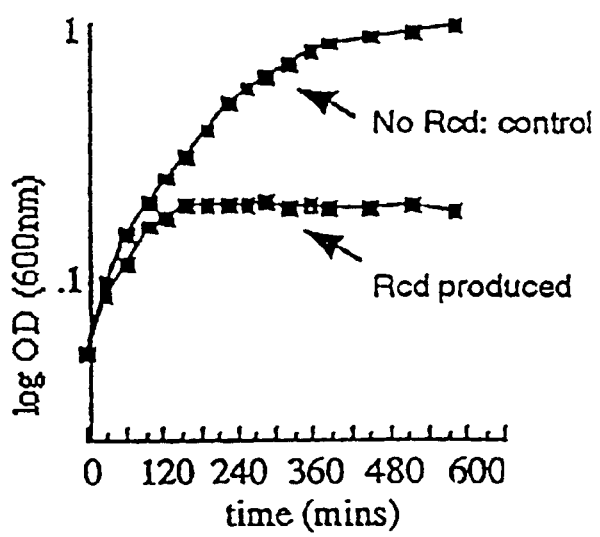

FIG. 6 illustrates the use of plasmids B8 and pC1857 to induce quiescence in *E. coli* strain DS941 hns. Within two hours of the induction of rcd, the optical density of the culture stops increasing. The optical density of a control culture in which Rcd is not expressed continues to increase until the cells reach stationary phase.

Figure 7:
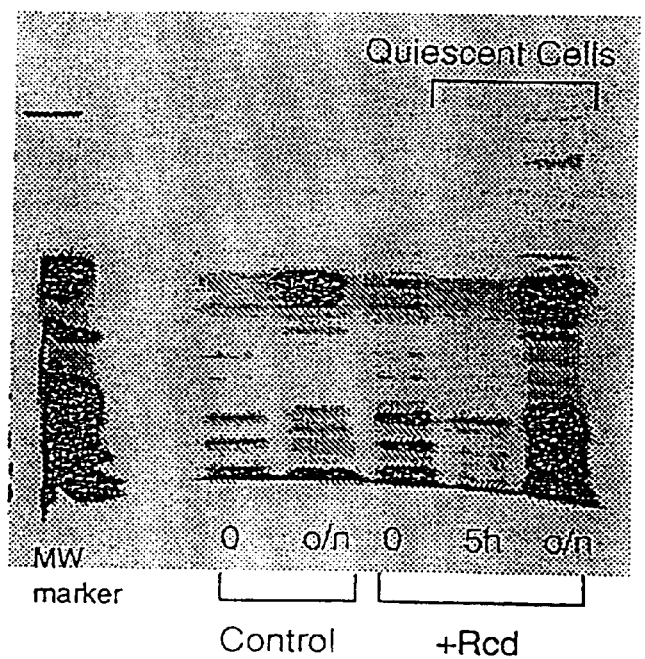

FIG. 7 illustrates protein synthesis in a culture made quiescent by the induction of rcd (+Rcd) at t=0. Protein synthesis continues strongly 5 hours and 20 hours (o/n) after the induction of rcd. The control lanes show protein synthesis in a normal (non-quiescent) culture.

Figure 8:
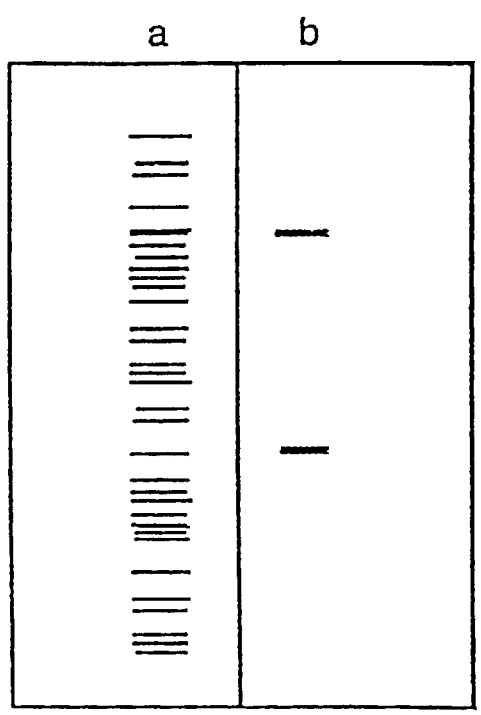

FIGS. 8A and 8B illustrate the identification of plasmid-encoded protein by SDS-PAGE. ³⁵S methionine is incorporated into proteins synthesised by cells after rcd induction.

FIG. 8a illustrates the results obtained by analysing total cell protein of cells in the absence of Rcd expression.

FIG. 8b illustrates the result obtained by autoradiography of Rcd expressing cells: only plasmid-encoded proteins are produced and appear on the autoradiograph.

Figure 9:
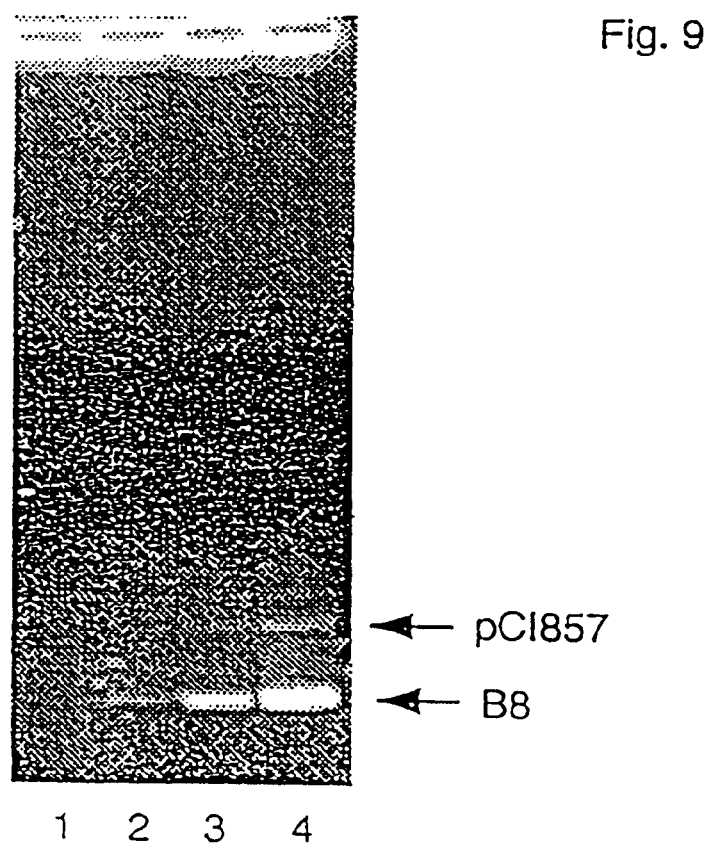

FIG. 9 illustrates the amplification of plasmid copy number in quiescent cells. Rcd synthesis was induced in a culture of DS941 hns cells carrying plasmids B8 and pCI857. Plasmid DNA was prepared from equal volumes of culture 2, 4, 7, and 20 hours after the induction of Rcd (lanes 1, 2, 3 and 4, respectively). The optical density of the culture did not increase significantly during this time so the increasing brightness of the plasmid bands (arrowed) reflects an increase in copy number.

Figure 10:
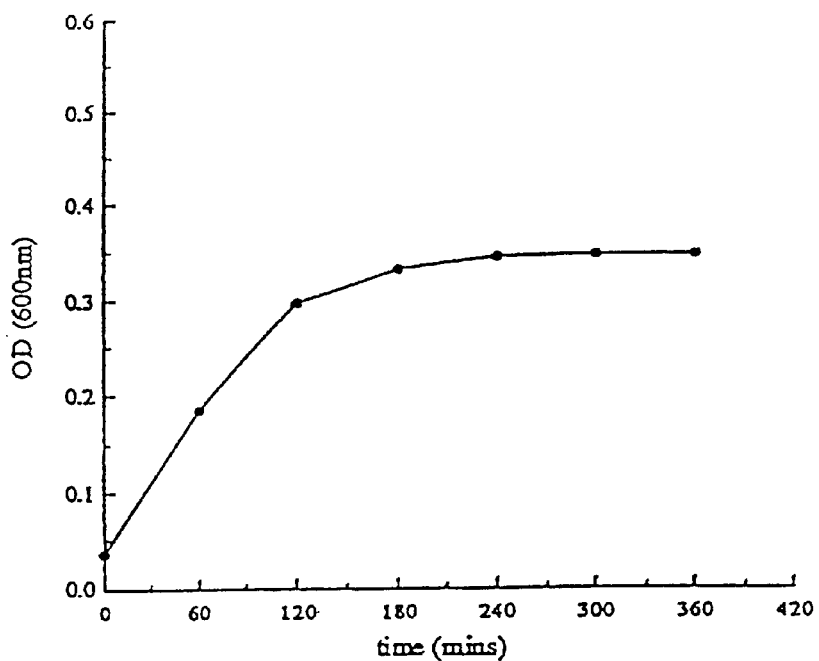

FIG. 10 shows entry of a culture of DS941hns-205 pCII-B8-12 cells into quiescence in response to induction of Rcd at t=0.

Figure 11:
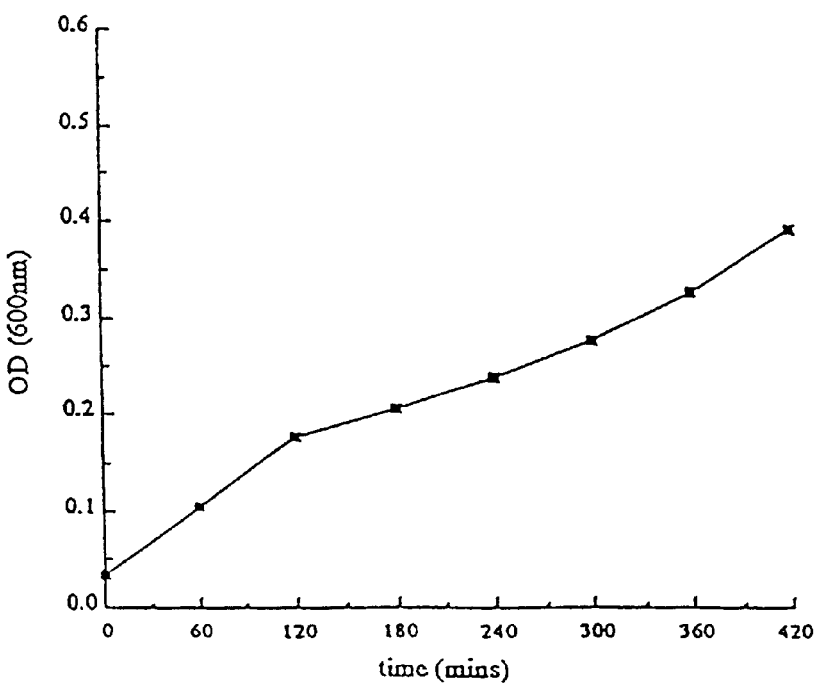

FIG. 11 shows a culture of DS94hns-205 containing plasmids pCII-B8-12 & pSC1 fails to enter quiescence in response to Rcd induction at t=0. pSC1 produces H-NS to complement the chromosomal mutation.

FIGS. 12A–12C shows the kinetics of growth of DS941 containing different hns alleles in the presence and absence of Rcd. FIG. 12(a) and 12(b) show results obtained with alleles which produce an N-terminal truncated polypeptide. The allele used in the experiment of which the results are given in FIG. 12(c) shows a complete loss of the H-NS polypeptide.

Figure 13:
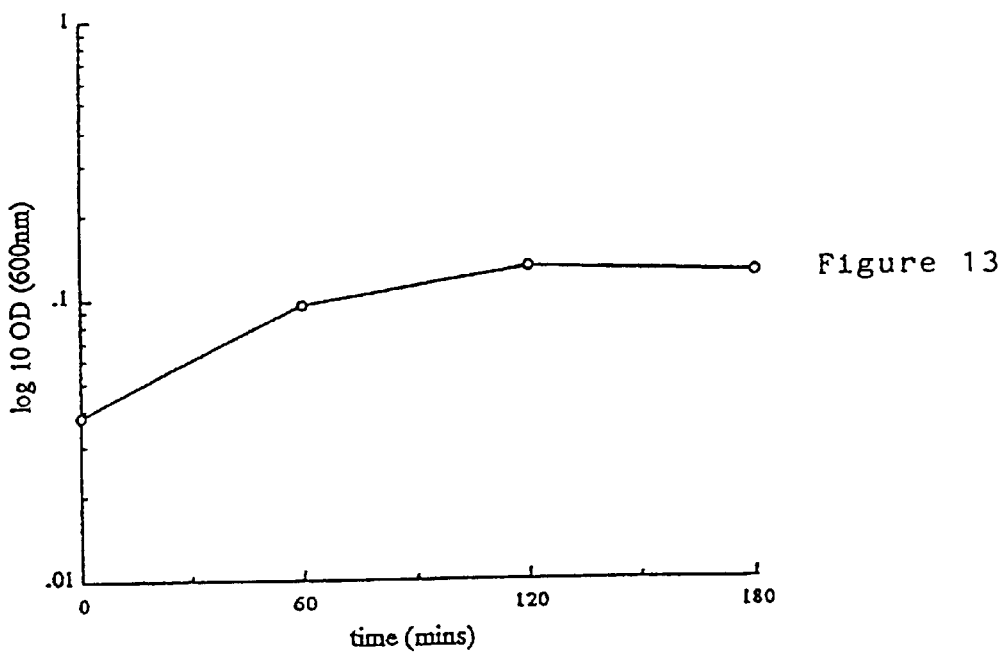

FIG. 13 shows growth kinetics of DS941hns-205 pGPlacZ B8 during entry into quiescence.

Figure 14:
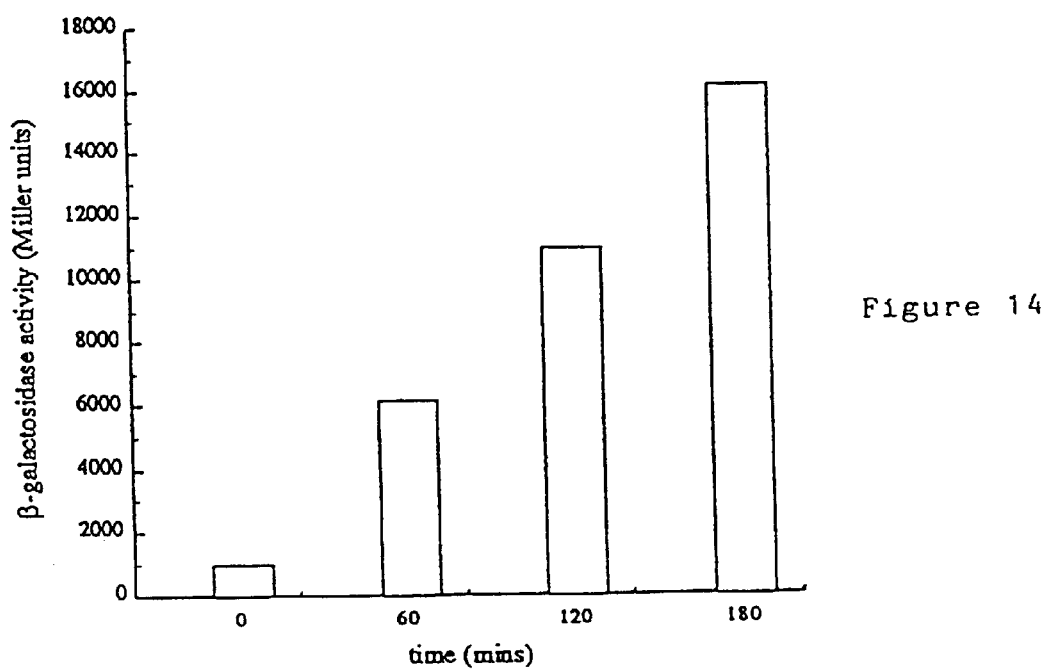

FIG. 14 shows β-galactosidase activity expressed from the plasmid-borne lacZ gene in DS941hns-205 pGPlacZ B8 during entry into quiescence.

Figure 15:
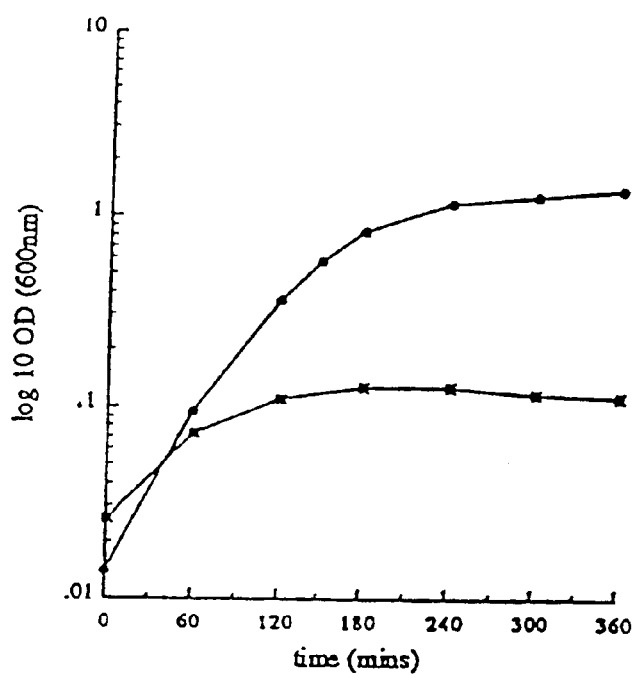

FIG. 15 shows growth curves for DS903hns-205 at 42° C., with (squares) or without (circles) over-expression of Rcd. The control culture enters stationary phase after approx. 240 min.

Figure 16:
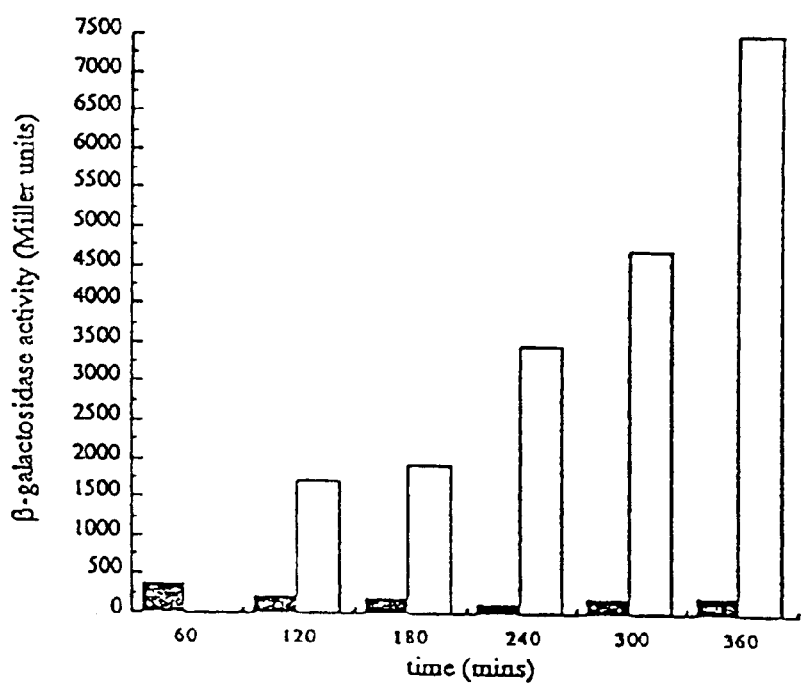

FIG. 16 shows β-galactosidase activity of the chromosomal lacZ gene of DS903hns-205 in the presence (black bars) and absence (white bars) of Rcd during selective batch culture at 42° C.

All references mentioned in the text are hereby incorporated by reference.

Those skilled in the art are well aware of methods which can be employed to generate hns⁻ or other mutant strains of *E. coli* or equivalents for other bacteria. One well-known technique which is particularly suitable is the use of "P1 transduction" (Miller 1972) to move transposon-inactivated hns. The technique involves introducing into host cells, via phage P1 infection, a defective hns gene containing an inserted transposon which includes a selectable marker (e.g. a gene which confers antibiotic resistance). Recombination within cells results in the replacement of the wild-type hns gene with the transposon-inactivated gene. Selection for the marker enables identification of successful recombination events. Only when the transposon is inserted into the host chromosome is the host-positive for the marker. Selected cells are tested for H-NS⁻ phenotype and suitability for use in the present invention (Rcd sensitivity).

We have primarily used the hns⁻ derivative of a strain (DS941) which had been shown already to be Rcd-sensitive (by testing on agar plates). Some mutational event in some laboratory strains has been found to cause some resistance to the effects of rcd. However, this in no way detracts from the generality of the present invention, since those strains which are useful in the invention can easily be identified using no more than routine trial and error.

EXAMPLE 1

ESTABLISHMENT OF QUIESCENCE

Rcd Expression Constructs

Figure 5:
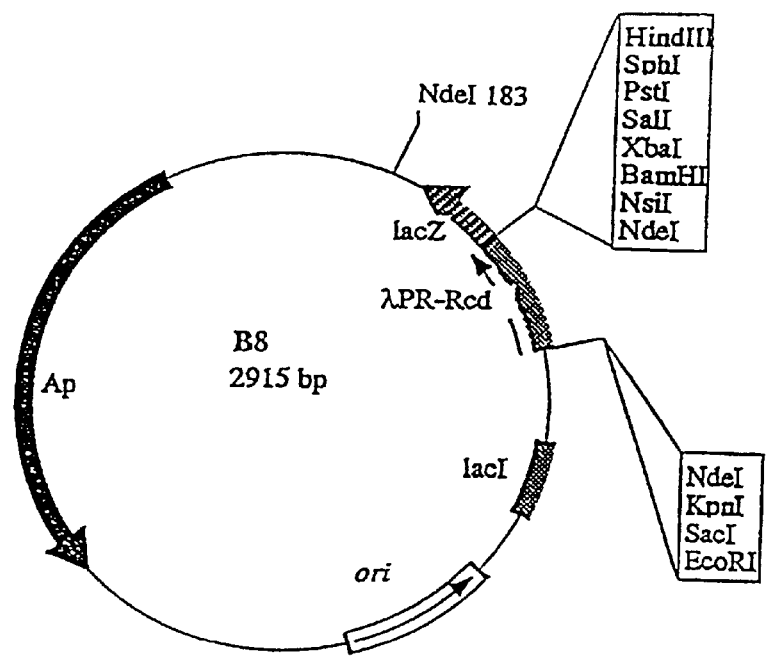
Figure 5:
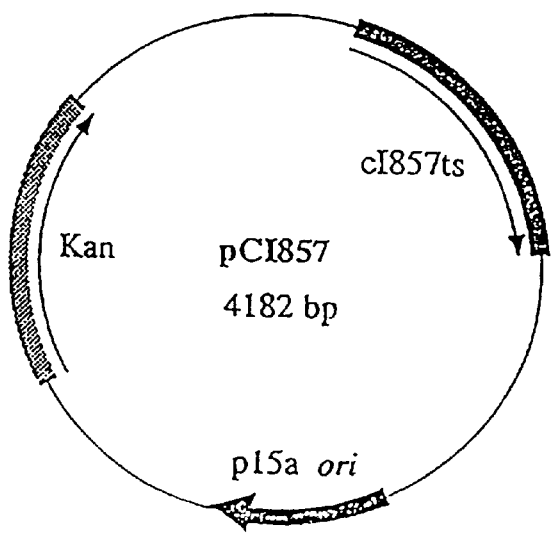

Using PCR technology we have made pUC-based plasmid constructs in which rcd is under the control of a modified $P_{lac}$ promoter or lambda $P_R$ promoter. The primers used in these constructions and the sequences of the Rcd cassettes are shown in FIG. 4a and FIG. 4b. A two-plasmid system used to induce quiescence is illustrated in FIG. 5. Plasmid B8 contains an Rcd expression cassette with rcd expressed from the lambda $P_R$ promoter. The promoter is regulated by the cI857 repressor protein which is expressed from plasmid pCI857 which is resident in the same cell. In the example illustrated in FIG. 5, synthesis of Rcd is induced by a temperature shift which inactivates the CI857 temperature sensitive repressor. In a cassette in which rcd is transcribed from $P_{lac}$ induction requires the addition of 1 mM IPTG to the growth medium.

The Establishment of the Quiescent State

FIG. 6 shows the growth of an L-broth culture of *E. coli* DS941 hns-205 containing plasmids B8 and pCI857 (FIG. 5). After growing exponentially for several generations, the culture was shifted from 30° C. to 42° C. (t=0) to induce Rcd expression. From 2 hours after the temperature shift there was no further increase in optical density (OD) of the culture in which Rcd was expressed. The OD remained constant for at least 20 hours (not shown). In a control culture, DS941 hns-205 carried a pUC18 plasmid without the Rcd cassette. This culture did not enter quiescence.

Protein Synthesis During Quiescence

We investigated protein synthesis in quiescent cells using $^{35}S$ methionine pulse-chase experiments. FIG. 7 is representative of data which we have obtained to date. As for the experiment illustrated in FIG. 6, the host strain was DS941 hns-205 containing plasmids B8 and pCI857. rcd was under the control of lambda $P_R$ and was induced by a temperature shift at t=0 to inactivate the lambda repressor. A 30 min pulse of $^{35}S$ methionine followed by an unlabelled chase (i.e. the addition of an excess of unlabelled amino acidy was performed at t=0, t=5 h or after overnight incubation (t=20 h approx.). After 5 h, the quiescent culture clearly showed non-uniform labelling of proteins. The strong band (arrowed) co-migrates with the plasmid-encoded cI857 lambda repressor. Even after overnight incubation, the quiescent cells remained extremely active in protein synthesis, compared to the control culture which had entered stationary phase by this time. The result is particularly striking because equal volumes of culture were used to prepare the two o/n tracks and the density of the control culture was approximately four times that of the quiescent culture. This demonstrates that quiescent cells maintain their capacity for protein synthesis.

EXAMPLE 2

PLASMID REPLICATION IN QUIESCENT CELLS

FIG. 9 shows an agarose gel of plasmid DNA purified from a culture during quiescence. Plasmid DNA was prepared from 1.5 mls of cells in L-broth and dissolved in a final volume 20 μl TE. 10 μl was loaded for each sample onto a 0.8% w/v agarose gel containing RNAse A (20 μg/ml final conc.). The gel was run for 2 hours at 50V. The host strain was DS941 hns containing B8 and pCI857 (FIG. 5). Cells were grown initially at 30° C. in L-broth. 3ml of culture was used to inoculate 17 ml L-broth pre-warmed to 42° C. Lane 1 shows plasmid DNA isolated after 2 h when the cells had just entered quiescence. Lane 2 shows plasmid DNA isolated after 4 h (i.e. 2 h into quiescence). Lane 3 shows plasmid DNA isolated after 7 h (5 h into quiescence). Lane 4 shows plasmid DNA isolated from the culture after incubation overnight. The density of the culture remained constant during the experiment so the increase in brightness of the plasmid bands reflects an increase in plasmid copy number in quiescent cells.

EXAMPLE 3

H-NS INVOLVEMENT IN ESTABLISHING QUIESCENCE

For rapid entry into the quiescent state and stable maintenance of this state, a host strain in accordance with embodiments of the present invention carries an hns mutation. Our normal hns allele (hns-205) results from a transposon insertion and such mutations are known to have polar effects on the expression of genes downstream in the operon. To demonstrate that it is the loss of function of hns (as opposed to the loss of a gene downstream of hns) which is involved in establishment of the quiescent state, we compared the effect of Rcd over-expression on cells carrying a chromosomal hns-205 mutation with or without a multicopy plasmid expressing wild-type H-NS. We found that where H-NS was provided from the plasmid, the cells failed to enter the quiescent state. Thus it is the inactivation of the hns itself (and not a downstream gene) which is involved in the establishment of quiescence in accordance with embodiments of the present invention.

Experimental

Bacteria and Plasmids: DS941 is a derivative of *E. coli* K-12 strain AB1157 (Bachman, (1972) *Bacteriol. Revs.*, 36, 525–557). DS941 is AB1157 recF lacI$^q$ lacZΔM15 and its hns-205::Tn10 derivative was constructed by P1 transduction from strain GM230 (Higgins, et al. (1988) Cell, 52, 569–584) selecting for mucoid, tetracycline resistant transductants. DS941 hns-205 was electroporated with plasmid pCIIT-B8-12 which expresses Rcd from the $\lambda P_R$ promoter and plasmid pSC1 which expresses of H-NS from the $P_{tac}$ promoter (McGovern et al., (1994) Biochimie, 76, 1019–1029). Transformants were selected on iso-sensitest agar at 30° C, supplemented with kanamycin (40 μgml$^{-1}$) to select for pCIIT-B8-12, ampicillin (100 μgml$^{-1}$) to select for pSC1 and glucose (0.1% w/v) to repress the $P_{tac}$ promoter. Plasmid pCIIT-B8-12 was constructed in 3 steps: (1) the 1098 bp BglII-PstI fragment of pCI857 was ligated to the 2900 bp BamHI-PstI fragment of pGP1-2 (Tabor & Richardson (1985) PNAS, 82, 1074–1078) to create pCII857. (2) The 1098 bp FspI fragment of pKK232-8 (Pharmacia), containing tandem rrnT2T1 terminators was then cloned into the unique, blunt-ended, PstI site of pCII857 to create pCII857T. (3) Finally, the 187 bp EcoRI-HindIII fragment of plasmid B8 was blunt-ended and ligated into the unique PvuII site of pCII857T between the two rrnBT2T1 terminators to create pCIIT-BB-12.

Cell Culture: Cells were grown in batch culture using 50 ml conical shake-flasks in L-broth (Kennedy, (1971) J. Bacteriol., 108, 10–19) containing kanamycin (40 μgml$^{-1}$) to select for pCIIT-B8-12 and, where appropriate, ampicillin (200gml$^{-1}$) to select for pSC1. Single colonies of DS941 hns-205 containing plasmids pCIIT-B8-12 and pSC1 were picked from selective plates and cultured overnight in 2 ml L broth at 30° C. 1 ml of the overnight culture was used to inoculate 20 ml L broth prewarmed to 30° C. After the cells had undergone several generations in exponential phase (reaching an OD$_{600\ nm}$ of 0.15), 4 ml of culture were withdrawn and used to inoculate 16 ml of L-broth prewarmed to 42° C. 20 μl of ampicillin (100 μgml$^{-1}$) were added each hour to maintain selection for pSC1. The shift in growth temperature to 42° C. induces Rcd expression from the $\lambda P_R$ promoter as the temperature sensitive CI$^{857}$ repressor protein is inactivated. Expression of the H-NS gene from the $P_{tac}$ promoter was not induced with IPTG as over expression of H-NS is lethal to the cell. Instead, cells were grown at 42° C. without addition of glucose to the L-broth so that catabolite repression of the promoter was lifted. Uninduced expression from the $P_{tac}$ promoter was. sufficient to produce sub-lethal levels of H-NS protein. In the control experiment single colonies of DS941 hns-205 pCIIT-B8-12 were picked from plates containing kanamycin (50 µgml$^{-1}$) and tetracycline (5 µgml$^{-1}$) and cultured overnight in 2 ml L broth at 30° C. 0.5 ml of the DS941 hns-205 pCIIT-B8-12 overnight culture was used to inoculate 20 ml L-broth prewarmed to 30° C. After the cells had undergone several generations in exponential phase, reaching an OD$_{600nm}$ of 0.19, 3 ml of culture were withdrawn and used to inoculate 17 ml of L broth prewarmed to 42° C.

Cell Growth: Cell growth was followed by measuring the optical density of the culture at 600 nm.

Results

Induction of Rcd expression from the plasmid pCIIT-B8-12 generated quiescent DS941 hns-205 cells in the control experiment (FIG. 10). Beyond 120 minutes there was very little increase in optical density of the culture. However, when H-NS was expressed from pSC1, the effect of Rcd on cell growth was nullified (FIG. 11). The culture continued to grow well beyond the point at which cells lacking the H-NS-producing plasmid entered a quiescent state.

Conclusion

Expression of H-NS from a plasmid prevents cells from entering a quiescent state when Rcd is over-expressed. We conclude that it is the loss of chromosomal hns expression, rather than interference with the expression of genes downstream of hns, which is involved in the establishment and maintenance of quiescence in accordance with embodiments of the present invention.

EXAMPLE 4

ESTABLISHMENT OF THE QUIESCENT STATE USING DIFFERENT hns ALLELES

For rapid establishment of a quiescent culture a bacterial strain in accordance with the present invention carries an hns mutation. We have compared the efficacy of various hns alleles in the establishment of the quiescent state. We show that cells carrying hns alleles which produce partially-functional, truncated H-NS protein enter the quiescent state more rapidly than cells carrying an hns null allele (i.e. where no H-NS protein is detectable by Western blotting).

Experimental

Bacteria and Plasmids: DS941 is a derivative of E. coli K-12 strain AB1157 (Bachman, (1972) Bacteriol. Revs., 36, 525–557). Specifically, DS941 is AB1157 recF lacI$^q$ lacZΔM15 and hns derivatives were constructed by P1 transduction of the appropriate hns allele from (i) strain GM230 (Higgins, et al. (1988) Cell, 52, 569–584) to construct an hns-205::Tn10 (ii) strain N43 (Prof. B. Holland, Université Paris-Sud) to construct hns::Tn10(N43) and (iii) strain PD32 (Dersch, et al., Mol. Gen. Genet. (1994) 245, 255–259) to construct hns-206::Amp. The hns-205::Tn10 and hns::Tn10(N43) alleles produce a truncated H-NS protein. Cells carrying these mutations were selected as mucoid, tetracycline (5–10 gml$^{-1}$) resistant colonies at 30° C. The hns-206::Amp allele is a null mutation. Cells carrying the hns-206::Amp allele were selected as yellow, mucoid colonies on salicin and bromothymol blue indicator plates (Schnetz, et al., (1987) J. Bacteriol., 169, 2579–2590) containing ampicillin (50 µgml-1) at 37° C.

Construction of Plasmid pCIIT-B8-12: pCIIT-B8-12 is a plasmid containing rcd under the control of λP$_R$ and also expressing the temperature sensitive cI$^{857}$ lambda repressor. It was constructed in 3 steps: (1) the 1098 bp BglII-PstI fragment of pC1857 was ligated to the 2900 bp BamHI-PstI fragment of pGP1-2 (Tabor & Richardson (1985) PNAS, 82, 1074–1078) to. create pCII857. (2) The 1098 bp FspI fragment of pKK232-8 (Pharmacia), containing tandem rrnBT2T1 terminators was then cloned into the unique, blunt-ended, PstI site of pCII857 to create pCII857T. (3) Finally, the 187 bp EcoRI-HindIII fragment of plasmid B8 was blunt-ended and ligated into the unique PvuII site of pCII857T between the two rrnBT2T1 terminators to create pCIIT-B8-12.

Strain Construction: DS941 hns-206 was electroporated with plasmid pCIIT-B8-12 which provides expression of Rcd from the λP$_R$ promoter. Transformants were selected on iso-sensitest agar supplemented with kanamycin (40 µgml$^{-1}$) and ampicillin (50 µgml$^{-1}$) at 30° C. DS941 hns::Tn10(N43) and DS941 hns-205 were electroporated with plasmid pCI857 (Remaut et al., (1983) Gene, 22, 103–113) and plasmid B8 (pUC18::λP$_R$-Rcd). Transformants were selected on iso-sensitest agar supplemented with kanamycin (10–50 µgml$^{-1}$) and ampicillin (100 µgml$^{-1}$) and tetracycline (5–15 µgml$^{-1}$) at 30° C.

Cell Culture: Cells were grown in batch culture using 50 ml conical shake-flasks in L-broth (Kennedy, (1971) J. Bacteriol., 108, 10–19) containing kanamycin (40–50 µgml$^{-1}$) to select for pCIIT-B8-12 and pCI857 , ampicillin or carbencillin (200 µgml$^{-1}$) to select for plasmid B8. Single colonies were picked from selective plates and cultured overnight in 2–3 ml L broth at 30° C. 0.5–1 ml of the overnight cultures was used to inoculate 20 ml L broth prewarmed to 30° C. After the cells had undergone several generations in exponential phase (reaching an OD$_{600nm}$ of 0.1–0.29), 1–3 ml of culture were withdrawn and used to inoculate 16–19 ml of L broth prewarmed to 42° C. 20 µl of ampicillin (100 µgml$^{-1}$) were added each hour to maintain selection for plasmid B8. The shift in growth temperature to 42° C. induces Rcd expression from the λP$_R$ promoter as the temperature sensitive CI$^{857}$ repressor protein is inactivated.

Cell Growth: Cell growth was followed by measuring the optical density of the culture at 600 nm.

Results

Figure 12:
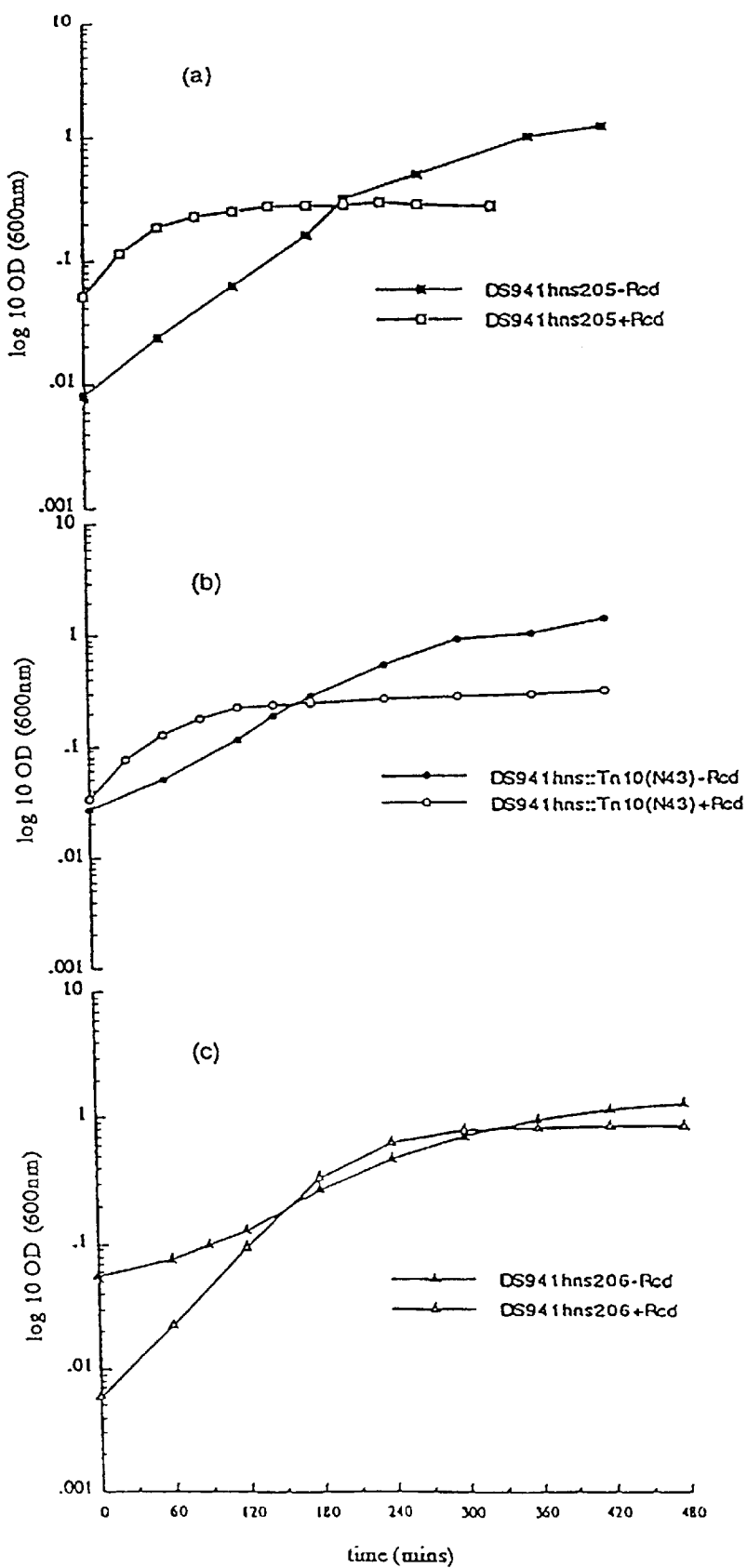

A comparison of the three graphs in FIG. 12 shows that the DS941 hns-206 culture, (carrying the hns null mutation), does not enter the quiescent state on induction of Rcd expression as rapidly as the two truncated hns alleles. DS941 hns-205 and DS941 hns::Tn10(N43) cultures, carrying different hns alleles which both produce a truncated version of the H-NS protein, enter a quiescent state within 120 minutes of induction of Rcd expression.

Conclusion

A bacterial strain with an hns allele which produces a truncated H-NS rotein may be particularly suitable for achieving an Rcd-induced quiescent state.

EXAMPLE 5

QUANTIFICATION OF PLASMID GENE EXPRESSION IN QUIESCENT CELLS

The aim of this experiment was to demonstrate gene expression in quiescent cells from a promoter used routinely in molecular biology. We have measured the expression of a plasmid-borne lacZ gene (whose product is β-galactosidase) expressed from a lambda promoter (λP$_L$) in a quiescent culture of strain DS941hns-205::Tn10. We show that cells in quiescence can both transcribe and translate the plasmid-based gene.

Experimental

Bacteria and Plasmids: DS941 is a derivative of *E. coli* K-12 strain AB1157 (Bachman, (1972) Bacteriol. Revs., 36, 525–557). Specifically, DS941 is AB1157 recF lac$^q$ lacZΔM15 and its hns-205::Tn10 derivative was constructed by P1 transduction of the hns allele from strain GM230 (Higgins, et al. (1988) Cell, 52, 569–584) selecting for mucoid, tetracycline resistant colonies. DS941hns-205 was electroporated with plasmid pGPlacZ (Rowe and Summers). This plasmid was constructed by ligating the 3414 bp AseI-HindIII fragment of plexlacz (Invitrogen) to the 3950 bp BamHI-EcoRI fragment of pGP1-2 (Tabor & Richardson (1985) PNAS, 82, 1074–1078). Both fragments were blunt-ended using Klenow polymerase. Plasmid pGPlacZ contains the lacZ gene under control of the $\lambda P_L$ promoter and the CI$^{857}$ temperature sensitive repressor gene under control of the $P_{lac}$ promoter. Transformants were selected at 30° C. on iso-sensitest agar supplemented with kanamycin (20 μgml$^{-1}$) to select for pGPlacZ, IPTG (1 mM) to ensure production of the CI repressor and tetracycline (10 μgml$^{-1}$) to select for the hns-205 allele. DS941hns-205 pGPlacZ was then electroporated with plasmid B8 which contains rcd under control of the $\lambda P_R$ promoter on a PCR generated fragment (Rowe and Summers, unpublished) cloned into the SmaI site of pUC18 (Vieira & Messing, (1982) Gene, 19, 259–268.). Transformants were selected at 30° C. on iso-sensitest agar supplemented with kanamycin (20 μgml$^{-1}$), IPTG (1 mM) and ampicillin (100 μgml$^{-1}$). Prior to the experiment the plasmid-bearing strain was cultured under conditions that repress lacZ and rcd expression (30° C. and addition of 1 mM IPTG to the medium).

Cell Culture and the Establishment of Quiescence: Cells were grown in L-broth (Kennedy, (1971) J. Bacteriol, 108, 10–19) containing kanamycin (40 μgml$^{-1}$) and ampicillin (200 μgml$^{-1}$) for plasmid selection, 1 mM IPTG to induce expression of the CI repressor, and tetracycline (10 μgml$^{-1}$) for selection of the hns-205 allele. A single colony of DS41hns-205 containing plasmids pGPlacZ and B8 was picked from selective plates and cultured overnight in 2 ml L-broth at 30° C. 0.5 ml of the overnight culture was used to inoculate 20 ml L-broth prewarmed to 30° C. After the cells had undergone several generations in exponential phase, reaching an OD$_{600\ nm}$ of 0.23–0.26, 3 ml of culture were withdrawn and used to inoculate 17 ml of L-broth (without IPTG) prewarmed to 42° C. 20 μl of carbencillin (50 μgml$^{-1}$) were added each hour to maintain selection for plasmid B8. The shift in growth temperature induced both rcd and lacz expression from the $\lambda P_R$ and $\lambda P_L$ promoters, respectively (the CI$^{857}$ protein does not function as a transcriptional repressor at 42° C.).

β-galactosidase (LacZ) Expression in Quiescent Cells: Cell growth was followed by measuring the optical density (OD) of the culture at 600 nm. Expression of the LacZ gene was followed by assaying β-galactosidase activity using the method of Miller (Miller, J. (1972) Experiments in Molecular Genetics. Cold Spring Harbor, New York, Cold Spring Harbor Laboratory Press). β-galactosidase activity was expressed in Miller units which are equivalent to the increase in σ-nitrophenol per minute per bacterium.

Results

FIG. 13 shows the effect of rcd and lacZ induction on bacterial growth. The culture entered into the quiescent state and there was no further increase in OD$_{600}$ after 120 min. FIG. 14 shows the change in β-galactosidase activity in these cells following Rcd over-expression. It is evident that during entry into quiescence, and after quiescence was established, there was both transcription and translation of lacZ from the $\lambda P_L$ promoter. β-galactosidase activity continued to increase over the 120 to 180 minute time period when there was no increase in OD$_{600\ nm}$. (Note that the density of the culture is taken into account in the calculation of β-galactosidase activity so that, irrespective of changes in optical density, an increase in enzyme units indicates an increase in active β-galactosidase per cell in the culture.)

Conclusion

Quiescent cells in broth culture are capable of both transcription and translation of a plasmid-borne gene.

EXAMPLE 6

CHROMOSOMAL GENE EXPRESSION IS DEPRESSED IN QUIESCENT CELLS

Good expression of a plasmid-borne lacZ has been demonstrated (see Example 5). Here we show that there is very poor expression of a chromosomal lacZ gene even in the presence of IPTG (a gratuitous inducer of the lac operon). We do this by comparing expression of the gene in strain DS903hns-205::Tn10 in the presence and absence of Rcd.

Experimental

Bacteria and Plasmids: DS903 is a derivative of *E. coli* K-12 strain AB1157 (Bachman (1972) Bacteriol. Revs., 36, 525–557). Specifically DS903 is AB1157 recF and carries a wild-type lacZ gene. An hns-205::Tn10 derivative of DS903 was constructed by P1 transduction from strain GM230 (Higgins, et al. (1988) Cell, 52, 569–584) selecting for mucoid, tetracycline resistant colonies. DS903hns-205 was electroporated with plasmids pCI857 (Remaut et al., (1983) Gene, 22, 103–113) and plasmid BB (pUC18::$\lambda P_R$-Rcd). Transformants were selected at 30° C. on iso-sensitest agar supplemented with kanamycin (50 μgml$^{-1}$), carbencillin (100 μgml$^{-1}$), IPTG (1 mM) and tetracycline (10 μgml$^{-1}$)

Cell Culture and Quiescence: Cells were grown in batch culture using 50 ml conical shake-flasks in L-broth (Kennedy, (1971) J. Bacteriol., 108, 10–19) containing antibiotics, where appropriate, for plasmid selection, and tetracycline for selection of the hns-205 allele. Single colonies of DS903hns-205 (control) and DS903hns-205 containing plasmids pCI857 & B8 were picked from selective plates and cultured overnight in 3 ml L-broth at 30° C. 1 mM IPTG was present throughout the experiment in the culture medium of the plasmid-containing strain. 0.3 ml of the DS903hns-205 overnight culture was used to inoculate 20 ml L-broth containing 1 mM IPTG pre-warmed to 42° C., to induce lacZ expression. To generate a quiescent culture, 0.2 ml of the overnight culture of DS903hns-205 containing plasmids CIB57 & B8 was inoculated into 20 ml L-broth prewarmed to 30° C. After the cells-had undergone several generations in exponential phase Treaching an OD$_{600\ nm}$ of 0.18) 3 ml of culture were withdrawn and used to inoculate 17 ml of L-broth prewarmed to 42° C. 20 μl of carbencillin (50 μgml$^{-1}$) were added each hour to maintain selection for plasmid B8. The shift in growth temperature makes cells quiescent by induction of rcd expression from the $\lambda P_R$ promoter. The CI$^{857}$ repressor protein does not function at 42° C.

Cell Growth and LacZ Expression: Cell growth was followed by measuring the optical density of the cultures at 600 nm. Expression of the lacZ gene was followed by assaying β-galactosidase activity using the method of Miller (Miller, J. (1972) Experiments in Molecular Genetics. Cold Spring Harbor, New York, Cold Spring Harbor laboratory Press). β-galactosidase activity was expressed in Miller units which are equivalent to the increase in σ-nitrophenol per minute per bacterium.

Results

The effect of Rcd expression on the growth of DS903hns-205 containing pCI857 and B8 is shown in FIG. 15. After 120 minutes no new biomass was generated (i.e. cells had entered a quiescent state). The control DS903hns-205 grown at 42° C. shows a conventional growth curve, entering stationary phase after 360 minutes at 42° C. (FIG. 15). The maximum level of β-galactosidase expression from the chromosomal lacZ gene (expressed from $P_{lac}$ promoter) in the quiescent culture was less than 500 Miller units (FIG. 16). By contrast, the control culture DS903hns-205, which lacked the Rcd plasmid, showed a much higher level of β-galactosidase activity, increasing to over 7,000 Miller units during the experiment (FIG. 16).

Conclusion

These results demonstrate that expression of a chromosomal gene is depressed in quiescent cells. In accordance with the present invention, a gene would need to be vector-borne in order to be expressed well in quiescent cells. Furthermore, this experiment demonstrates that chromosomal gene expression is very different in (non-growing) quiescent cells from that in cells which have stopped growing due to entry into stationary phase. In the former case levels of the gene product decline while in the latter they rise. This emphasises the difference between quiescence and stationary phase.

EXAMPLE 7

LARGE SCALE PREPARATION OF CLONED GENE PRODUCTS

A small culture of DS941hns containing plasmids of the type shown in FIG. 5 is prepared under conditions which are non-inducing for Rcd. This is used to seed a large-scale culture which is induced for Rcd synthesis and for expression of the heterologous gene in mid-late logarithmic phase. The culture is then maintained under inducing conditions to allow expression of the cloned gene. The time of Rcd induction and the length of the period for which the cells remain quiescent before harvesting need to be optimised for individual host-vector combinations and culture conditions. Such optimisation will be routine for those skilled in the art.

EXAMPLE 8

MONITORING THE PRODUCTION OF PLASMID GENE PRODUCTS

A $^{35}$S-labelled amino acid (typically methionine) is added to a culture of cells after they have been made quiescent by Rcd induction (i.e. soon after t=2 h in FIG. 6). Radioactivity is incorporated preferentially into plasmid products (the chromosome being synthetically-inactive). The cells are then lysed and an SDS-polyacrylamide gel is used to separate total cellular protein (FIG. 8a). Autoradiography reveals which bands are plasmid-derived (FIG. 8b). For this particular case it is most convenient to use a stock of hns⁻ cells already containing a plasmid from which Rcd is expressed and introduce the test plasmid subsequently.

EXAMPLE 9

SYNCHRONISING DIVISION OF CELLS

To achieve synchrony, DS941hns cells containing a multicopy plasmid with a temperature- or chemically-inducible rcd gene are inoculated into broth and grown into exponential phase under non-inducing conditions. At an appropriate cell density, Rcd synthesis is induced and incubation continued for at least two cell generation times. It becomes more difficult to bring cells out of quiescence if they are left in a long time, so this is borne in mind in experimental design. The inducing signal (high temperature or chemical inducer) is then removed and the growth of the culture resumes. The cell cycles of cells in the culture are synchronised.

REFERENCES

1. Finkel & Johnson (1992). *Mol. Microbiol.*, 6(22), 3257–3265.
2. Gerdes et al (1990). *Mol. Microbiol.*, 4(11), 1807–1818.
3. Harris & Angal (Ed.) (1989). Protein purification methods. Oxford: IRL Press.
4. Miller (1972). In *Experiments in Molecular Genetics* (pp. 201–205). Cold Spring Harbor Laboratories.
5. Jaffe et al (1985). *J. Bacteriol.*, 163, 841–849.
6. Harris (Ed.) (1989). *Protein purification methods*. Oxford: IRL Press.
7. Patient & Summers (1993). *Mol. Microbiol.*, 8(5), 1089–1095.
8. Summers (1991). *Trends in Biotechnology*, 9(8), 273–278.
9. Summers et al (1993). *Mol. Microbiol.* 8(6), 1031–1038.
10. Summers & Sherratt (1984). *Cell*, 36, 1097–1103.
11. Summers & Sherratt (1988). *EMBO Journal*, 7(3), 851–858.
12. Xia et al (1991). *Mol. Microbiol.*, 5(3), 631–640.
13. Ussery et al (1994). *Biochimie*, 76, 968–980.
14. Nielsen & Molin (1984). *Plasmid*, 11, 264–267.
15. Old & Primrose (1994). *Principles of gene manipulation: an introduction to genetic engineering*. Oxford: Blackwell Scientific.
16. Remaut (1983). *Gene* 22, 103–113.
17. Court, D. (1993). RNA processing and degradation by RNase III. In Belasco, J. & Brawerman, G. (eds), *Control of Messenger RNA Stability*. Academic Press, Inc., New York., 71–117.
18. Donovan et al. (1986) *Proc. Natl. Acad. Sci. USA*, 83, 120–124.
19. Söderbom et al. (1997) Swedish PhD thesis ('Structure, function and metabolic stability of antisense RNAs, Uppsala Universitet, Sweden).
20. Tomcsányi, T. & Apirion, D. (1985) *J. Mol. Biol.*, 185, 713–720.
21. Xu et al. (1993) *Proc. Natl. Acad. Sci. USA*, 90, 6756–6760.

What is claimed is:

1. A bacterial cell containing a first extra-chromosomal vector including an inducible rcd gene, which cell when in broth culture enters quiescence on expression of the rcd gene.

2. A cell according to claim 1 containing a second extra-chromosomal vector, said vector comprising a heterologous gene.

3. A cell according to claim 2 wherein the heterologous gene is under the control of an inducible promoter.

4. A cell according to claim 3 wherein the inducible rcd gene and the inducible promoter of said heterologous gene are inducible by application of the same stimulus.

5. A cell according to claim 2 wherein the heterologous gene, when expressed, produces a product which adversely affects viability, cell growth and/or cell division of the cell.

6. A cell containing a first extra-chromosomal vector according to claim 1 wherein the first extra-chromosomal vector further comprises a heterologous gene.

7. A cell according to claim 1 which is an *E. coli* cell.

Figure 1:
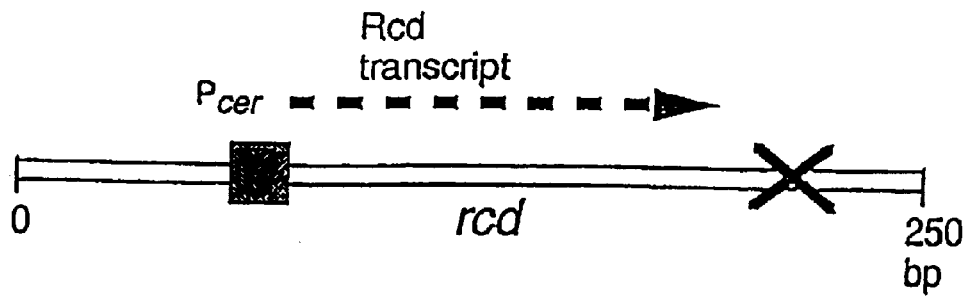
Figure 2:
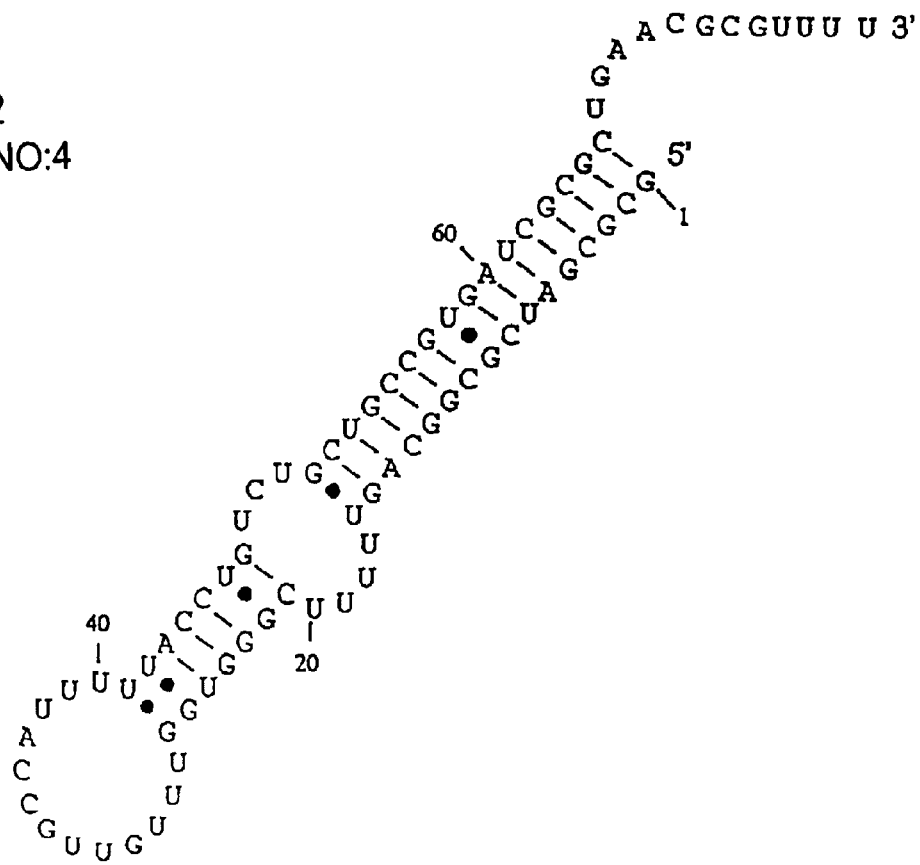
FIG. 2 shows the sequence and structure of the rcd transcript RNA (SEQ ID NO. 4).

8. A cell according to claim 1 wherein the rcd gene is *E. coli* rcd for which the transcribed RNA sequence is shown in FIG. 2 (SEQ ID NO:2).

9. A cell according to claim 1 which is hns⁻.

10. A cell according to claim 1 in a broth culture.

11. A cell according to claim 10 in which Rcd is being expressed from the inducible rcd gene and which cell is quiescent.

12. A method of producing a cell according to claim 2, the method comprising introducing into a bacterial cell containing a first extra-chromosomal vector including an inducible rcd gene, which cell when in broth culture enters quiescence on expression of the rcd gene, a second extra-chromosomal vector which includes a heterologous gene, thereby producing said cell according to claim 2.

13. A method for inducing quiescence in a cell according to claim 1 comprising growing said cell in broth culture and inducing rcd expression to cause the cell to enter quiescence.

14. A method for expressing a heterologous gene comprising growing a cell according to claim 6 in broth culture, inducing rcd expression to cause the cell to enter quiescence, and
causing or allowing expression of said heterologous gene.

15. A method according to claim 14 wherein expression of said heterologous gene is induced when rcd expression is induced.

16. A method according to claim 14 wherein expression of said heterologous gene is induced after the cell enters quiescence.

17. A method according to claim 15 wherein expression of said heterologous gene is induced when rcd expression is induced.

18. A method according to claim 15 wherein expression of said heterologous gene is induced after the cell enters quiescence.

19. A method according to claim 15 including isolating and/or purifying from the broth culture the expression product of said heterologous gene.

20. A method according to claim 15 including isolating and/or purifying from one or more cells taken from the broth culture the expression product of said heterologous gene.

21. A method wherein, after isolation and/or purification of an expression product in accordance with claim 19 the expression product is modified.

22. A method wherein, after isolation and/or purification of an expression product in-accordance with claim 19 the expression product or a modified form thereof is included in a composition which includes at least one additional component.

23. A method of monitoring expression from an extra-chromosomal vector of interest, the method comprising
  introducing the vector of interest into a cell according to claim 1,
  growing the cell in broth culture,
  inducing rcd expression,
  causing or allowing expression from the vector of interest, and
  determining expression from the vector of interest in the cell, thereby monitoring expression from the vector of interest.

24. A method according to claim 23 wherein mRNA is determined.

25. A method according to claim 23 wherein polypeptide is determined.

26. A method according to claim 25 wherein polypeptide expression is determined by gel electrophoresis.

27. A method according to claim 23 wherein the cell is an *E. coli* cell.

28. A method according to claim 23 wherein the rcd gene is *E. coli* rcd for which the transcribed RNA sequence is shown in FIG. 2.

29. A method according to claim 23 wherein the cell is hns.

30. A method wherein, after amplification of the copy number of an extra-chromosomal vector of interest in a bacterial cell in accordance with a method of claim 28. the extra-chromosomal vector of interest is isolated and/or purified from the broth culture or one or more cells taken from the broth culture.

31. A method for amplifying the copy number of an extra-chromosomal vector of interest in a bacterial cell, the method comprising introducing the vector of interest into a cell according to claim 1, growing the cell in broth culture, and causing the cell to enter quiescence by inducing rcd expression, the copy number of said vector increasing during and after entry into quiescence.

32. A method for isolating and/or purifying an extra-chromosomal vector comprising amplifying the copy number of an extra-chromosomal vector of interest in a bacterial cell in accordance with a method of claim 31, and isolating and /or purifying the extra-chromosomal vector of interest from the broth culture or one or more cells taken from the broth culture.

33. A method according to claim 23 wherein the cell or cells are *E coli*.

34. A method according to claim 23 wherein the rcd gene is *E. coli* rcd for which the transcribed RNA sequence is shown in FIG. 2.

35. A method according to claim 23 wherein the rcd gene is a mutant, derivative, variant or homologue of the rcd gene for which the transcribed RNA sequence is shown in FIG. 2, by way of addition, substitution, deletion and/or insertion of one or more nucleotides, which mutant, derivative, variant or homologue has the ability to cause a bacterial cell in broth culture to enter quiescence.

* * * * *

SEQUENCE LISTING

<160> NUMBER OF SEQ ID NOS: 11

<210> SEQ ID NO 1
<211> LENGTH: 29

-continued

```
<212> TYPE: DNA
<213> ORGANISM: Escherichia coli
<220> FEATURE:
<221> NAME/KEY: promoter
<222> LOCATION: (1)..(29)
<220> FEATURE:
<221> NAME/KEY: mutation
<222> LOCATION: (7)..(23)
<223> OTHER INFORMATION: temperature sensitive, 42 degrees C permissive
      temperature

<400> SEQUENCE: 1
ttgttgcata ggtattcata cggtaaaat                                          29

<210> SEQ ID NO 2
<211> LENGTH: 12
<212> TYPE: DNA
<213> ORGANISM: Escherichia coli

<400> SEQUENCE: 2
cgggtggttt gt                                                            12

<210> SEQ ID NO 3
<211> LENGTH: 12
<212> TYPE: RNA
<213> ORGANISM: Escherichia coli

<400> SEQUENCE: 3
cgggugguuu gu                                                            12

<210> SEQ ID NO 4
<211> LENGTH: 78
<212> TYPE: RNA
<213> ORGANISM: Escherichia coli

<400> SEQUENCE: 4
gcgcgaucgc ggcaguuuuu cggugguuu guugccauuu uuaccugucu gcugccguga         60
ucgcgcugaa cgcguuuu                                                      78

<210> SEQ ID NO 5
<211> LENGTH: 64
<212> TYPE: DNA
<213> ORGANISM: Escherichia coli

<400> SEQUENCE: 5
atgcatatgg cttgacaatt gtgagcgata acaattataa tgtgtggagg cgcgatcgcg        60
gcag                                                                     64

<210> SEQ ID NO 6
<211> LENGTH: 49
<212> TYPE: DNA
<213> ORGANISM: Escherichia coli

<400> SEQUENCE: 6
atgcatatga atttgtgagc gataacaatt gatttaccat aatcccttta                   49

<210> SEQ ID NO 7
<211> LENGTH: 75
<212> TYPE: DNA
<213> ORGANISM: Escherichia coli

<400> SEQUENCE: 7
atgcatatgt aacaccgtgc gtgttgacta ttttacctct ggcggtgata atggttgcag        60
```

```
gcgcgatcgc ggcag                                                       75
```

<210> SEQ ID NO 8
<211> LENGTH: 24
<212> TYPE: DNA
<213> ORGANISM: Escherichia coli

<400> SEQUENCE: 8

```
atgcatatga tttaccataa tccc                                             24
```

<210> SEQ ID NO 9
<211> LENGTH: 191
<212> TYPE: DNA
<213> ORGANISM: Artificial Sequence
<220> FEATURE:
<223> OTHER INFORMATION: Description of Artificial Sequence:
      Nucleotides 1-49 are the E. coli P-lac promoter, and
      nucleotides 50-127 encode the E. coli rcd
      transcript
<220> FEATURE:
<221> NAME/KEY: promoter
<222> LOCATION: (1)..(49)
<220> FEATURE:
<221> NAME/KEY: misc_RNA
<222> LOCATION: (50)..(127)

<400> SEQUENCE: 9

```
atgcatatgg cttgacaatt gtgagcgata acaattataa tgtgtggagg cgcgatcgcg      60
gcagtttttc gggtggtttg ttgccatttt tacctgtctg ctgccgtgat cgcgctgaac     120
gcgttttagc ggtgcgtaca attaagggat tatggtaaat caattgttat cgctcacaaa    180
atcatatgca t                                                          191
```

<210> SEQ ID NO 10
<211> LENGTH: 169
<212> TYPE: DNA
<213> ORGANISM: Artificial Sequence
<220> FEATURE:
<223> OTHER INFORMATION: Description of Artificial Sequence:
      Nucleotides 1-49 are the E. coli P-lac promoter, and
      nucleotides 50-127 encode the E. coli rcd
      transcript.
<220> FEATURE:
<221> NAME/KEY: promoter
<222> LOCATION: (1)..(49)
<220> FEATURE:
<221> NAME/KEY: misc_RNA
<222> LOCATION: (50)..(127)
<220> FEATURE:
<221> NAME/KEY: promoter
<222> LOCATION: (1)..(60)
<220> FEATURE:
<221> NAME/KEY: misc_RNA
<222> LOCATION: (61)..(138)

<400> SEQUENCE: 10

```
atgcatatgg cttgacaatt gtgagcgata acaattataa tgtgtggagg cgcgatcgcg      60
gcagtttttc gggtggtttg ttgccatttt tacctgtctg ctgccgtgat cgcgctgaac     120
gcgttttagc ggtgcgtaca attaagggat tatggtaaat catatgcat                 169
```

<210> SEQ ID NO 11
<211> LENGTH: 180
<212> TYPE: DNA
<213> ORGANISM: Artificial Sequence
<220> FEATURE:
<223> OTHER INFORMATION: Description of Artificial Sequence:
      Nucleotides 1-60 are the E. coli bacteriophage lambda
      promoter, and nucleotides 61-138 encode the E.

```
                                coli rcd transcript.

<400> SEQUENCE: 11
atgcatatgt aacaccgtgc gtgttgacta ttttacctct ggcggtgata atggttgcag        60
gcgcgatcgc ggcagttttt cgggtggttt gttgccattt ttacctgtct gctgccgtga      120
tcgcgctgaa cgcgttttag cggtgcgtac aattaaggga ttatggtaaa tcatatgcat      180
```